US008968591B2

(12) United States Patent
Nishikubo et al.

(10) Patent No.: US 8,968,591 B2
(45) Date of Patent: Mar. 3, 2015

(54) ORGANIC PIEZOELECTRIC MATERIAL, ULTRASOUND TRANSDUCER, ULTRASOUND PROBE, AND ULTRASOUND MEDICAL DIAGNOSTIC IMAGING SYSTEM

(75) Inventors: Yuichi Nishikubo, Kanagawa (JP); Rie Fujisawa, Kanagawa (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 588 days.

(21) Appl. No.: 13/321,476

(22) PCT Filed: Feb. 23, 2010

(86) PCT No.: PCT/JP2010/052720
§ 371 (c)(1),
(2), (4) Date: Nov. 18, 2011

(87) PCT Pub. No.: WO2010/137366
PCT Pub. Date: Dec. 2, 2010

(65) Prior Publication Data
US 2012/0065516 A1    Mar. 15, 2012

(30) Foreign Application Priority Data

May 25, 2009   (JP) ................................. 2009-125098
Jun. 29, 2009   (JP) ................................. 2009-153580

(51) Int. Cl.
| H01L 41/08 | (2006.01) |
| H01L 41/193 | (2006.01) |
| H01L 41/22 | (2013.01) |
| H04R 17/00 | (2006.01) |
| A61B 8/00 | (2006.01) |
| C08K 5/00 | (2006.01) |
| G01S 7/52 | (2006.01) |
| H01L 41/45 | (2013.01) |

(52) U.S. Cl.
CPC ............... *H01L 41/193* (2013.01); *A61B 8/00* (2013.01); *C08K 5/0008* (2013.01); *G01S 7/52017* (2013.01); *G01S 7/52019* (2013.01); *H01L 41/45* (2013.01)
USPC ...... 252/62.9 R; 600/459; 524/169; 524/210; 524/211; 524/212; 310/322; 310/334

(58) Field of Classification Search
USPC .............. 252/62.9 R; 600/459; 310/322, 334; 524/169, 210, 211, 212
See application file for complete search history.

(56) References Cited

FOREIGN PATENT DOCUMENTS

| JP | 02-284485 | 11/1990 |
| JP | 5-311399 | 11/1993 |

(Continued)

OTHER PUBLICATIONS

A. Leo, Comprehensive Medicinal Chemistry, vol. 4, C. Hansch, P.G. Sammens, J.B. Taylor and C. A. Ramsden, Eds., p. 295, Pergamon Press, 1990.

*Primary Examiner* — Carol M Koslow
(74) *Attorney, Agent, or Firm* — Lucas & Mercanti, LLP

(57) ABSTRACT

Disclosed is an organic piezoelectric material which has excellent piezoelectric characteristics and excellent handling properties. Also disclosed are an ultrasound transducer using the organic piezoelectric material, an ultrasound probe, and an ultrasound medical diagnostic imaging system. Specifically disclosed is an organic piezoelectric material which contains a base material that is formed from a resin, and a specific compound (1) that has at least one linking group selected from among specific linking groups. The organic piezoelectric material is characterized in that the relation shown below is satisfied when the CLogP values of the specific compound (1) and the base material are respectively represented by CLogP(1) and CLogP(base material). Relation: |CLogP(1)−CLogP(base material)|≤3.0.

8 Claims, 2 Drawing Sheets

(56) References Cited

FOREIGN PATENT DOCUMENTS

| | | |
|---|---|---|
| JP | 6-216422 | 8/1994 |
| JP | 2004-349386 | 12/2004 |
| JP | 2007-329334 | 12/2007 |
| JP | 2008-279114 | 11/2008 |
| JP | 2008-304223 | 12/2008 |
| WO | 2005/026144 | 3/2005 |
| WO | 2009-025145 | 2/2009 |

ORGANIC PIEZOELECTRIC MATERIAL, ULTRASOUND TRANSDUCER, ULTRASOUND PROBE, AND ULTRASOUND MEDICAL DIAGNOSTIC IMAGING SYSTEM

This application is a U.S. National Phase Application under 35 USC 371 of International Application PCT/JP2010/052720 filed Feb. 23, 2010, which in turn claimed the priority of Japanese Patent Application Nos. 2009-125098 filed May 25, 2009, and JP2009-153580, all three of the applications are incorporated by reference herein.

FIELD OF THE INVENTION

The present invention relates to an organic piezoelectric material having excellent piezoelectric characteristics, an ultrasound transducer and an ultrasound probe and an ultrasound medical diagnostic imaging system using thereof.

TECHNICAL BACKGROUND

Heretofore, organic piezoelectric material having piezoelectric and pyroelectric performances was well-known which can transduce thermal or mechanical stimulation into electric energy, and can be employed as audio equipment such as diaphragm for microphone or speaker, various heat sensor, pressure sensor, or instruments such as infrared detector, ultrasound probe, and vibration sensor having high sensitivity for detecting such as variation of gene or protein.

As piezoelectric and pyroelectric materials, employed are so called inorganic piezoelectric materials prepared by polarizing treatment of single crystal such as crystal, $LiNbO_3$, $KNbO_3$; thin film such as ZnO or AlN; and sintered body such as $Pb(Zr, Ti)O_3$. These piezoelectric materials of inorganic composition have features of high elastic stiffness, high mechanical loss coefficient, high density and high dielectric constant.

On the other hand, also developed are organic piezoelectric materials such as polyvinylidene fluoride (hereinafter, referred to as "PVDF") or polycyano vinylidene (hereinafter, referred to as "PVDCN") (for example, Patent Document 1). As organic piezoelectric material has features such that workability for thin film or large area is excellent, arbitrary shape and form can be easily formed, and elasticity and dielectric constant is low, thereby it has feature to enable high sensitive detection when it is employed for sensor use.

Since organic piezoelectric material looses piezoelectric and pyroelectric property due to its low heat resistance as well as reducing physical property such as elastic stiffness at high temperature, it has limitations to applicable temperature range.

With respect to resolve these limitation, variously investigated were polyurea resin composition comprising urea bond as organic piezoelectric material, because it has large dipole moment at urea bond and exhibits excellent temperature characteristics as resin.

For example, disclosed was a so called deposition polymerization method in which polyurea film was formed by depositing isocyanate compound such as 4,4'-diphenylmethane diisocyanate (MDI) and diamine compound such as 4,4'-diamino diphenyl methane (MDA) simultaneously (for example, Patent Documents 2 and 3). However, since polyurea resin composition formed by the described deposition polymerization method has un-uniform molecular weight of formed olygomer or polymer, when polymerization was performed while polarizing treatment, polyurea resin composition was formed in a state of insufficient orientation. Therefore, it is difficult to utilize dipole moment of urea bond effectively, thereby further improvement was required to organic piezoelectric materials.

Dendrimer compound is a collective term of branched polymer having regular dendritic branches detailed in documents such as Hawker, C. J. et al: J. Chem. Soc., Chem. Commun., 1990, 1010; Tomalia, D. A. et al: Angew. Chem. Int. Ed. Engl., vol: 29, page: 138 (1990); Frech et. J. M. J.: Science, vol: 263, page: 1710 (1994), or Kakimoto Masaaki, Kagaku, vol: 50, page: 608 (1995). These molecules have polymer structure having regular branches from a center of molecule. Therefore, for example, as explained in above document by Tomalia, terminal of branches becomes extremely sterically-congested according to polymerization, resulting in forming spherically-extended molecular structure.

One of means for preparing piezoelectric material having high orientation is to introduce a polarizing group having high dipole moment into dendrimer compound to subject piezoelectricity. However, though there were reports of dendrimer compound having polarizing group (for example, Patent Document 4 and Non-Patent Document 1), examples related to piezoelectricity were not disclosed and there was no report related to dendrimer compound having enough performances as piezoelectric material. In view of the foregoing, the inventors of the present invention conducted investigations, and as a result, found that dendrimer can be employed as piezoelectric material.

However, when dendrimer was singly employed, it was found that there remained room for improvement in view of film forming and handling. Therefore, dendrimer would be employed by mixing with other base material having excellent film forming property. However, it was found that mixing with base material having low compatibility (large difference between ClogPs) caused phase separation between materials, resulting in low piezoelectricity and being difficult in applying to sensor described before, due to acoustic scattering caused at boundary.

Further, on the other hand, in an investigation of an organic piezoelectric material which has liquid crystal property by utilizing high dipole moment of urea bond, the inventor of the present invention found that organic material having liquid crystal property can be employable as piezoelectric material.

However, organic piezoelectric material having urea group had poor film forming property and also extremely bad handling. Therefore, organic piezoelectric material having urea group would be employed by mixing with other base material having excellent film forming property. However, it was found that mixing with base material having low compatibility (large difference between ClogPs) caused phase separation between materials, resulting in low piezoelectricity and being difficult in applying to sensor described before, due to acoustic scattering caused at boundary.

PRIOR TECHNICAL DOCUMENT

Patent Document

Patent Document 1: Unexamined Japanese Patent Application (hereinafter, refers to JP-A) No. 6-216422
Patent Document 2: JP-A No. 2-284485
Patent Document 3: JP-A No. 5-311399
Patent Document 4: WO 2005/026144

Non-Patent Document

Non-Patent Document 1: Angewandte Chemie International Edition, vol. 47, 5175-5178, 2008

SUMMARY

Problems to be Solved by the Present Invention

In view of the foregoing, the inventors of the present invention conducted diligent investigations. An object of the present invention is to provide an organic piezoelectric material which has excellent piezoelectric characteristics and excellent handling properties. Also provided are an ultrasound transducer using the organic piezoelectric material, an ultrasound probe, and an ultrasound medical diagnostic imaging system.

Means to Solve the Problems

The above object has been attained by the following constitutions:

1. An organic piezoelectric material comprising a compound having a substructure represented by Formula (1A) and a base material comprising a resin, wherein CLogP(1A) and CLogP(base material) satisfies a relation represented by Expression (1), provided that CLogP(1A) represents ClogP value of the compound having the substructure and CLogP (base material) represents ClogP value of the base material,

Ar-(L-X—W)$_m$,  Formula (1A)

wherein Ar represents an aromatic hydrocarbon ring or an aromatic heterocyclic ring, X represents —NR$_1$C(=O)NR$_2$—, —NR$_1$C(=S)NR$_2$—, —OC(=O)O—, —OC(=S)O—, —NHC(=O)O—, —NHC(=S)O—, —NHC(=O)—, —NHC(=S)—, —SO$_2$NH—, or —NHSO$_2$NH—, L represents a linking group or a single bond, R$_1$ and R$_2$ each represents hydrogen atom or a substituent group independently, W represents a substituent group, and m represents an integer of 2-8, and

|CLogP(1A)−CLogP(base material)|≤3.0,  Expression (1)

wherein ClogP represents "Calculated LogP" derived by Fragment approach of Hansch and Leo.

2. The organic piezoelectric material of item 1, wherein Ar is an aromatic hydrocarbon ring or an aromatic heterocyclic ring selected from benzene, benzoquinone, anthracene, triphenylene, truxene, tricycloquinaqzoline and dibenzopyrene.

3. The organic piezoelectric material of any one of items 1 to 2, wherein L in Formula (1A) is a single bond.

4. An organic piezoelectric material comprising a compound represented by Formula (1B) or a polymer having a residual group of the compound represented by Formula (1B) in a side chain through Q$_1$ or Q$_2$, and a base material comprising a resin, wherein CLogP(1B) and CLogP(base material) satisfies a relation represented by Expression. (2), provided that CLogP(1B) represents ClogP value of the compound or the polymer and CLogP(base material) represents ClogP value of the base material,

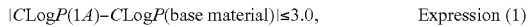

Q$_1$-A$_1$-(L$_1$-A$_1$)$_n$-Q$_2$,  Formula (1B)

wherein A$_1$ represents —NR$_1$C(=O)NR$_2$—, —NR$_1$C(=S)NR$_2$—, OC(=O)O—, —OC(=S)O—, —NHC(=O)O—, —NHC(=S)O—, —NHC(=O)—, —NHC(=S)—, —SO$_2$NH—, or —NHSO$_2$NH—; Q$_1$ and Q$_2$ each independently represents an un-substituted aromatic group, an aromatic group substituted by an alkyl group or an alkoxy group, or a cyclolkyl group substituted by an alkyl group or an alkoxy group; L$_1$ represents a divalent linking group, n represents an integer of 0-100; and R$_1$ and R$_2$ in A$_1$ each represents hydrogen atom or a substituent group independently, and

|CLogP(1B)−CLogP(base material)|≤3.0,  Expression (2)

wherein CLogP represents "Calculated LogP" derived by Fragment approach of Hansch and Leo.

5. The organic piezoelectric material of item 4, wherein Q$_1$ and Q$_2$ in Formula (1B) is an aromatic group having an alkoxy group.

6, The organic piezoelectric material of any one of items 1 to 5, wherein the resin constituting the base material is a thermoplastic resin, a thermosetting resin or a photo curable resin.

7. An ultrasound transducer comprising the organic piezoelectric material of any One of items 1 to 6.

8. An ultrasound probe providing the ultrasound transducer comprising the organic piezoelectric material of any one of items 1 to 6.

9. The ultrasound probe of item 8, wherein the ultrasound transducer is an ultrasound transducer for reception.

10. An ultrasound medical diagnostic imaging system providing the ultrasound probe comprising the organic piezoelectric material of any one of items 1 to 6,

Effects of the Invention

According to the present invention, it has become possible to provide an organic piezoelectric material which has excellent piezoelectric characteristics and excellent handling properties. Also provided are an ultrasound transducer, an ultrasound probe, and an ultrasound medical diagnostic imaging system using thereof.

PREFERRED EMBODIMENT OF THE INVENTION

Figure 1:
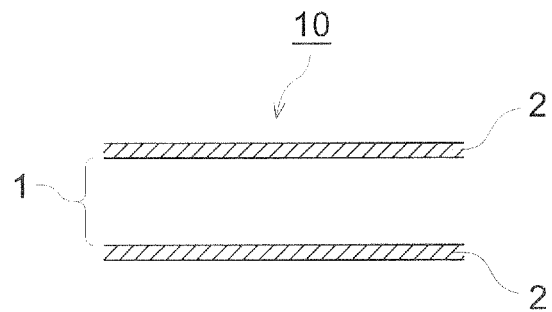
FIG. 1 is a schematic cross-sectional view showing the basic construction of an ultrasound transducer.

The organic piezoelectric material of the present invention is characterized in comprising the specific compound (1) which has at least one linking group selected from —NR$_1$C(=O) NR$_2$—, —NR$_1$C(=S)NR$_2$—, —OC(=O)O—, —OC(=S)O—, —NHC(=O)O—, NHC(=S)O—, —NHC(=O)—, —NHC(=S)—, —SO$_2$NH—, or —NHSO$_2$NH—, (herein, R$_1$ and R$_2$ each represents hydrogen atom or a substituent group independently), and the base material comprising a resin; and CLogP(1A) and CLogP (base material) satisfies a relation represented by the following Expression, provided that CLogP(1A) represents ClogP of the compound having a substructure and CLogP(base material) represents ClogP values of the base material,

|CLogP(1A)−CLogP(base material)|≤3.0,  Expression wherein ClogP represents "Calculated LogP" derived by Fragment approach of Hansch and Leo.

Herein, the specific compound (1) is referred to as a compound having a substructure represented by Formula (1A) or a compound represented by Formula (1B) or a polymer having a residual group of the compound represented by Formula (1B) in a side chain through Q$_1$ or Q$_2$, Above features are common technical characteristics in the inventions described herein.

In view of effecting the embodiment of the present invention, it is preferable that Ar in Formula (1A) is an aromatic hydrocarbon ring or an aromatic heterocyclic ring selected from benzene, benzoquinone, anthracene, triphenylene, truxene, tricycloquinaqzoline and dibenzopyrene, more preferable L in Formula (1A) is a single bond.

In the present invention, it is preferable that CLogP(1B) and CLogP(base material) satisfies a relation represented by Expression (2), provided that CLogP(1B) represents ClogP of the compound or the polymer having a residual group of the compound represented by Formula (1B) in a side chain through $Q_1$ or $Q_2$ and CLogP(base material) represents ClogP values of the base material, wherein $Q_1$ and $Q_2$ in Formula (1B) is preferable an aromatic group having an alkoxy group.

In the organic piezoelectric material of the present invention, the organic polymer material constituting the base material is preferable a thermoplastic resin, a thermosetting resin or a photo curable resin.

The organic piezoelectric material of the present invention is preferably employed to an ultrasound transducer, and the ultrasound transducer is preferably employed to an ultrasound probe. Herein, the ultrasound transducer is preferable an ultrasound transducer for reception.

Further, the ultrasound probe is preferably employed to an ultrasound medical diagnostic imaging system.

In the present invention, the term "CLogP" represents "Calculated LogP" derived by Fragment approach of Hansch and Leo. Herein, "CLogP" is a coefficient which represents an affinity of an organic compound to water and 1-octanol. In the partition equilibrium when the compound is dissolved as a solute into two liquid phase solvents of 1-octanol and water, 1-octanol/water partition coefficient P means a ratio of the equilibrium concentrations of the solute in the respective solvents. It is usually expressed in the form of "LoqP", that is, logarithm to the base 10. "LogP" for various compounds were reported. Various values are available and referred from data base such as Daylight Chemical Information Systems, Inc. (Daylight CIS). When a measured "LogP" value is unable, it can be calculated a conveniently by using program "CLOGP" available from Daylight CIS This program outputs a "calculated LogP(CLogP)" determined by the fragment approach of Hansch and Leo along with a measured LogP in case of existing. The fragment approach is based on the chemical structure of a compound by considering the number of atoms and the type of chemical bond as described in Reference: A. Leo, Comprehensive Medicinal Chemistry, Vol. 4, C. Hansch, P. G. Sammens, J. B. Taylor and C. A. Ramsden, Eds., p. 295, Pergamon Press, 1990. Since the "ClogP" is the most reliable and widely used estimate of a logP value, it enables to be used instead of the measured LogP value for selecting compound. In the present invention, either of the measured logP value or ClogP determined by calculation according to the program CLOGP v4.01 is usable, but ClogP value is used preferably as a standard. Further, in case of the base material comprising resin, value is calculated based on a unit structure (monomer) when an unit structure has molecular weight of 500 or more, or based on a multimer having molecular weight of 500 or more when molecular weight is 500 or less.

The present invention and the components and the embodiments thereof will now be detailed.

The present invention is characterized by employing a compound having a substructure represented by Formula (1A) or a compound represented by Formula (1B) or a polymer having a residual group of the compound represented by Formula (13) in a side chain through $Q_1$ or $Q_2$ as the specific compound (1). Each compound will now be detailed.

(Compound Represented by Formula (1A))

The organic piezoelectric material of the present invention is characterized in comprising a compound having a substructure represented by Formula (1A) and a base material comprising a resin.

$$\text{Ar-(L-X-W)}_m, \qquad \text{Formula (1A)}$$

wherein Ar represents an aromatic hydrocarbon ring or an aromatic heterocyclic ring.

As the aromatic hydrocarbon ring, a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, anthranthrene ring, a benzoquinone ring, an anthraquinone ring, a triphenylene ring, a truxene ring, and dibenzopyrene ring are cited for example.

As the aromatic heterocyclic ring, a furan ring, a thiophene ring, an oxazole ring, a pyrrole ring, a pyridine ring, a pyridazine ring, a pyrimidine ring, a pyrazine ring, a triazine ring, a benzoimidazole ring, a oxadiazole ring, a triazole ring, an imidazole ring, a pyrazole ring, a triazole ring, an indole ring, an indazole ring, a benzothiazole ring, a benzoxazole ring, a quinoxaline ring, a quinazoline ring, a cinnoline ring, a quinoline ring, an isoquinoline ring, a phthaladine ring, a naphthiridine ring, a carbazole ring, a carboline ring, a tricycloquinazoline ring, a diazacarbazole ring (a ring formed by replacing one of carbon atoms of a carboline ring by a nitrogen atom) can be cited, for example.

Ar is preferable a condensed ring having not less than 3 rings, more preferable not less than 4 rings. Specific examples of aromatic ring represented by Ar include following compounds Ar-1 to Ar-14.

| No. | Structure (* represents bond) |
|---|---|
| Ar-1 | |
| Ar-2 | |
| Ar-3 | |
| Ar-4 | |

| No. | Structure (* represents bond) |
|---|---|
| Ar-5 | |
| Ar-6 | |
| Ar-7 | |
| Ar-8 | |
| Ar-9 | |
| Ar-10 | |
| Ar-11 | |
| Ar-12 | |
| Ar-13 | |
| Ar-14 | |

L represents a linking group or a single bond. Linking group represented by L is preferable an aromatic group and a heterocyclic group, more preferable a phenylene group, a naphthylene group or a pyridilene group, further preferable a phenylene group. L is preferable a phenylene group or a single bond. Specific examples will be listed below.

| No. | Structure (* represents bond) |
|---|---|
| L-1 | |
| L-2 | |

| No. | Structure (* represents bond) |
|---|---|
| L-3 | 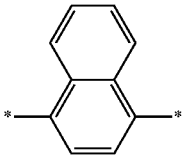 [SMILES: *c1ccc(*)c2ccccc12] |
| L-4 | 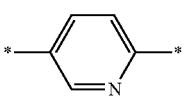 |
| L-5 | 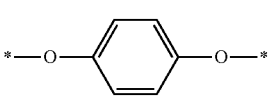 [SMILES: *Oc1ccc(O*)cc1] |

X represents —NR$_1$C(=O)NR$_2$—, —NR$_1$C(=S)NR$_2$—, —OC(=O)O—, —OC(=S)O—, —NHC(=O)O—, —NHC(=S)O—, —NHC(O)—, —NHC(=S)—, —SO$_2$NH—, or —NHSO$_2$NH—. Of these, —NR$_1$C(=O)NR$_2$—, —NR$_1$C(=S)NR$_2$—, and —NHSO$_2$NH— are preferably employed.

R$_1$ and R$_2$ each independently represents a hydrogen atom or a substituent. Specific examples of substituent include: alkyl group having 1-25 carbons (such as methyl group, ethyl group, propyl group, isopropyl group, t-butyl group, pentyl group, hexyl group, and cyclohexyl group), halogenated alkyl group (such as trifluoro methyl group, and perfluoro octyl group), cycloalkyl group (such as cyclohexyl group, and cyclopentyl group), alkynyl group (such as propagyl group), glycidyl group, acrylate group, methacrylate group, aromatic group (such as phenyl group), heterocyclic group (pyridyl group, thiazolyl group, oxazolyl group, imidazolyl group, furyl group, pyrrolyl group, pyrazinyl group, pyrimidinyl group, pyridazinyl group, selenazolyl group, sulfolanyl group, piperidinyl group, pyrazolinyl group, and tetrazolyl group), halogen atom (such as chlorine atom, bromine atom, iodine atom, and fluorine atom), alkoxy group (such as methoxy group, ethoxy group, propyloxy group, pentyloxy group, cyclopentyloxy group, hexyloxy group, and cyclohexyloxy group), aryloxy group (such as phenoxy group), alkoxy carbonyl group (such as methyloxy carbonyl group, ethyloxy carbonyl group, and butyloxy carbonyl group), aryloxy carbonyl group (such as phenyloxy carbonyl group), sulfonamide group (such as methane sulfonamide group, ethane sulfonamide group, butane sulfonamide group, and benzene sulfonamide group), sulfamoyl group (such as amino sulfonyl group, methylamino sulfonyl group, dimethylamino sulfonyl group, phenylamino sulfonyl group, and 2-pyridylamino sulfonyl group), urethane group (such as methyl ureido group, ethyl ureido group, cyclohexyl ureido group, phenyl ureido group, and 2-pyridyl ureido group), acyl group (acetyl group, propionyl group, butanoyl group, hexanoyl group, and benzoyl group), carbamoyl group (such as amino carbonyl group, methylamino carbonyl group, dimethylamino carbonyl group, propylamino carbonyl group, pentylamino carbonyl group, cyclohexylamino carbonyl group, phenylamino carbonyl group, and 2-pyridylamino carbonyl group), amide group (such as acetoamide group, propionamide group, butane amide group, and benzamide group), sulfonyl group (such as methyl sulfonyl group, ethyl sulfonyl group, butyl sulfonyl group, phenyl sulfonyl group, and 2-pyridyl sulfonyl group), amino group (such as amono group, ethyl amino group, dimethyl amino group, butyl amino group, and anilino group), cyano group, nitro group, sulfo group, carboxyl group, hydroxyl group, and oxamoyl group. These groups may be further substituted by these groups. Hydrogen atom or alkyl group having 1-10 carbons is preferable as a substituent represented by R$_1$ and R$_2$.

W represents a substituent. Specific examples for a substituent include the same specific examples listed as a substituents represented by R$_1$ and R$_2$. Of these, it is preferable aromatic group or heterocyclic group, more preferable aromatic group, and further preferable ones represented by following W-1 to W-4 (in Table, R represents a substituent, and preferably alkyl group having 1-20 carbons).

| No. | Structure (* represents bond) |
|---|---|
| W-1 | 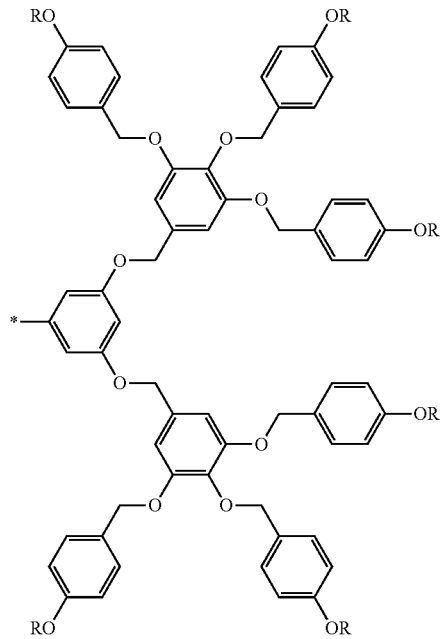 |
| W-2 | 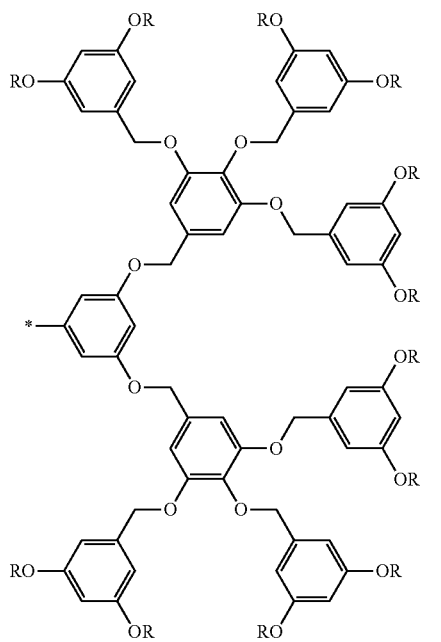 |

-continued

| No. | Structure (* represents bond) |
|---|---|
| W-3 | 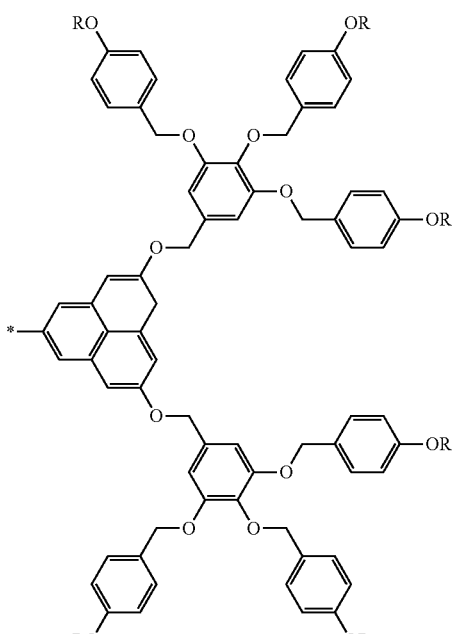 |
| W-4 | 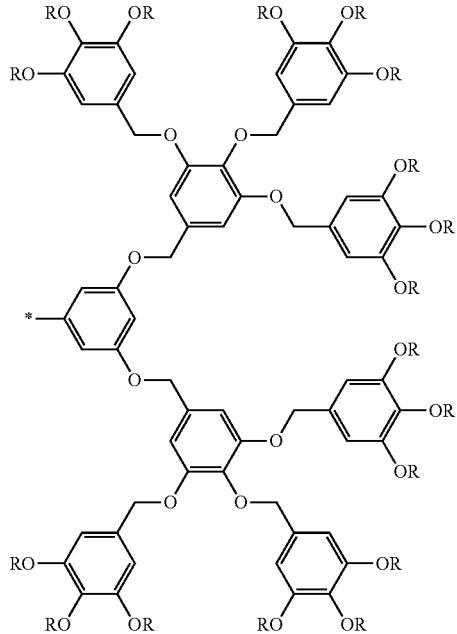 | m represents an integer of 2-8. A plurality of L, W, Q, $R_1$ and $R_2$ may be the same or different.

Specific examples of a compound represented by Formula (1A) are listed below, however the present invention is not limited thereto.

TABLE 1

| No. | Ar | m | L | X | $R_1$ | $R_2$ | Species of W | R |
|---|---|---|---|---|---|---|---|---|
| 1 | Ar-1 | 2 | Single bond | —$NR_1C(=O)NR_2$— | H | H | W-1 | $C_6H_{13}$ |
| 2 | Ar-1 | 2 | Single bond | —$NR_1C(=S)NR_2$— | H | H | W-2 | $C_{12}H_{25}$ |
| 3 | Ar-1 | 2 | Single bond | —OC(=O)O— | | | W-1 | $C_{10}H_{21}$ |
| 4 | Ar-1 | 2 | Single bond | —OC(=S)O— | | | W-2 | $C_{12}H_{25}$ |
| 5 | Ar-1 | 2 | L-1 | —$NR_1C(=S)NR_2$— | H | H | W-3 | $C_8H_{17}$ |
| 6 | Ar-2 | 2 | Single bond | —NHC(=O)O— | | | W-1 | $C_{12}H_{25}$ |
| 7 | Ar-2 | 2 | Single bond | —NHC(=S)O— | | | W-2 | $C_6H_{13}$ |
| 8 | Ar-2 | 2 | L-2 | —$NHSO_2NH$— | | | W-1 | $C_{12}H_{25}$ |
| 9 | Ar-2 | 2 | Single bond | —$NHSO_2NH$— | | | W-3 | $C_4H_9$ |
| 10 | Ar-2 | 2 | L-3 | —$NR_1C(=S)NR_2$— | $CH_3$ | H | W-4 | $C_6H_{13}$ |
| 11 | Ar-3 | 2 | Single bond | —$NR_1C(=S)NR_2$— | H | H | W-1 | $C_{12}H_{25}$ |
| 12 | Ar-3 | 2 | Single bond | —$NHSO_2NH$— | | | W-2 | $C_8H_{17}$ |
| 13 | Ar-3 | 2 | Single bond | —$NHSO_2NH$— | | | W-1 | $C_{12}H_{25}$ |
| 14 | Ar-3 | 2 | L-4 | —$NHSO_2NH$— | | | W-2 | $C_6H_{13}$ |
| 15 | Ar-3 | 2 | Single bond | —NHC(=O)— | | | W-4 | $C_4H_9$ |
| 16 | Ar-4 | 2 | Single bond | —NHC(=S)— | | | W-1 | $C_{12}H_{25}$ |
| 17 | Ar-4 | 2 | Single bond | —$SO_2NH$— | | | W-3 | $C_{10}H_{21}$ |
| 18 | Ar-4 | 2 | Single bond | —$NHSO_2NH$— | | | W-4 | $C_6H_{13}$ |
| 19 | Ar-4 | 2 | Single bond | —$NR_1C(=O)NR_2$— | H | H | W-1 | $C_8H_{17}$ |
| 20 | Ar-4 | 2 | Single bond | —$SO_2NH$— | | | W-1 | $C_4H_9$ |
| 21 | Ar-5 | 3 | Single bond | —$NR_1C(=O)NR_2$— | H | H | W-1 | $C_6H_{13}$ |
| 22 | Ar-5 | 3 | L-5 | —$SO_2NH$— | | | W-1 | $C_{12}H_{25}$ |
| 23 | Ar-5 | 3 | Single bond | —$NR_1C(=O)NR_2$— | H | H | W-2 | $C_{12}H_{25}$ |
| 24 | Ar-5 | 3 | Single bond | —$SO_2NH$— | | | W-3 | $C_4H_9$ |

TABLE 2

| No. | Ar | m | L | X | $R_1$ | $R_2$ | Species of W | R |
|---|---|---|---|---|---|---|---|---|
| 25 | Ar-5 | 3 | Single bond | —$SO_2NH$— | | | W-4 | $C_{12}H_{25}$ |
| 26 | Ar-6 | 2 | L-1 | —$NR_1C(=O)NR_2$— | H | H | W-1 | $C_{12}H_{25}$ |
| 27 | Ar-6 | 2 | Single bond | —$SO_2NH$— | | | W-2 | $C_6H_{13}$ |
| 28 | Ar-6 | 2 | L-1 | —$NR_1C(=S)NR_2$— | H | H | W-1 | $C_8H_{17}$ |
| 29 | Ar-6 | 2 | L-1 | —$NHC(=S)O$— | | | W-3 | $C_{12}H_{25}$ |
| 30 | Ar-6 | 2 | Single bond | —$NR_1C(=O)NR_2$— | H | H | W-4 | $C_6H_{13}$ |
| 31 | Ar-7 | 3 | Single bond | —$SO_2NH$— | | | $C_6H_{13}$ | — |
| 32 | Ar-7 | 3 | Single bond | —$NR_1C(=O)NR_2$— | H | H | $C_6H_{13}$ | — |
| 33 | Ar-7 | 3 | Single bond | —$NHC(=S)O$— | | | *$CH_2CH_2OOCCF_3$ | — |
| 34 | Ar-7 | 3 | Single bond | —$NR_1C(=S)NR_2$— | H | H | *$C_6H_{12}OC_2H_5$ | — |
| 35 | Ar-7 | 3 | Single bond | —$OC(=S)O$— | | | *$C_2H_4OC_{10}H_{21}$ | — |
| 36 | Ar-8 | 6 | Single bond | —$OC(=S)O$— | | | $C_8H_{17}$ | — |
| 37 | Ar-8 | 6 | Single bond | —$NHC(=S)O$— | | | $C_{14}H_{29}$ | — |
| 38 | Ar-8 | 6 | Single bond | —$NR_1C(=O)NR_2$— | H | H | $C_6H_{11}$ | — |
| 39 | Ar-8 | 6 | Single bond | —$SO_2NH$— | | | *$C_2H_4OC_8H_{17}$ | — |
| 40 | Ar-8 | 6 | Single bond | —$NR_1C(=S)NR_2$— | H | H | *$C_2H_4OC_8H_{17}$ | — |
| 41 | Ar-9 | 4 | Single bond | —$NR_1C(=O)NR_2$— | H | H | $C_8H_{17}$ | — |
| 42 | Ar-9 | 4 | Single bond | —$NR_1C(=S)NR_2$— | H | H | $C_6H_{13}$ | — |
| 43 | Ar-9 | 4 | Single bond | —$OC(=O)O$— | | | $C_{12}H_{25}$ | — |
| 44 | Ar-9 | 4 | Single bond | —$OC(=S)O$— | | | *$C_6H_{12}OC_2H_5$ | — |
| 45 | Ar-9 | 4 | L-1 | —$NR_1C(=S)NR_2$— | H | H | *$C_2H_4OC_8H_{17}$ | — |
| 46 | Ar-10 | 6 | Single bond | —$NHC(=O)O$— | | | $C_8H_{17}$ | — |
| 47 | Ar-10 | 6 | Single bond | —$NHC(=S)O$— | | | $C_{12}H_{25}$ | — |

TABLE 3

| No. | Ar | m | L | X | $R_1$ | $R_2$ | Species of W | R |
|---|---|---|---|---|---|---|---|---|
| 48 | Ar-10 | 6 | Single bond | —$NR_1C(=S)NR_2$— | H | H | $C_6H_{11}$ | — |
| 49 | Ar-10 | 6 | Single bond | —$NHSO_2NH$— | | | $C_6H_5$ | — |
| 50 | Ar-10 | 6 | L-3 | —$NR_1C(=S)NR_2$— | $CH_3$ | H | *$C_2H_4OC_6H_{13}$ | — |
| 51 | Ar-11 | 6 | Single bond | —$NR_1C(=S)NR_2$— | H | H | $C_4H_9$ | — |
| 52 | Ar-11 | 6 | Single bond | —$NHSO_2NH$— | | | *$C_2H_4OC_{12}H_{25}$ | — |
| 53 | Ar-11 | 6 | Single bond | —$NHSO_2NH$— | | | $C_6H_5$ | — |
| 54 | Ar-11 | 6 | L-4 | —$NHSO_2NH$— | | | *$C_2H_4OC_{12}H_{25}$ | — |
| 55 | Ar-12 | 6 | Single bond | —$NHC(=O)$— | | | *$C_2H_4OC_{12}H_{25}$ | — |
| 56 | Ar-12 | 6 | Single bond | —$NHC(=S)$— | | | $C_8H_{17}$ | — |
| 57 | Ar-12 | 6 | Single bond | —$SO_2NH$— | | | $C_{12}H_{25}$ | — |
| 58 | Ar-12 | 6 | Single bond | —$NHSO_2NH$— | | | $C_6H_{11}$ | — |
| 59 | Ar-12 | 6 | Single bond | —$NR_1C(=O)NR_2$— | H | H | *$C_2H_4OC_8H_{17}$ | — |
| 60 | Ar-12 | 6 | Single bond | —$SO_2NH$— | | | *$CH_2CH(CH_3)C_6H_{13}$ | — |
| 61 | Ar-12 | 6 | Single bond | —$NR_1C(=O)NR_2$— | H | H | $C_4H_7$ | — |
| 62 | Ar-13 | 6 | L-5 | —$SO_2NH$— | | | $C_{12}H_{25}$ | — |
| 63 | Ar-13 | 6 | Single bond | —$NR_1C(=O)NR_2$— | H | H | $C_5H_{11}$ | — |
| 64 | Ar-13 | 6 | Single bond | —$SO_2NH$— | | | *$CH_2OC_{10}H_{21}$ | — |
| 65 | Ar-13 | 6 | Single bond | —$SO_2NH$— | | | *$C_2H_4OC_{12}H_{25}$ | — |
| 66 | Ar-14 | 8 | Single bond | —$SO_2NH$— | | | $C_6H_{12}$ | — |
| 67 | Ar-14 | 8 | Single bond | —$SO_2NH$— | | | $C_6H_{11}$ | — |
| 68 | Ar-14 | 8 | Single bond | —$OC(=S)O$— | | | $C_6H_5$ | — |
| 69 | Ar-14 | 8 | L-1 | —$NHC(=S)O$— | | | *$C_2H_4OC_8H_{17}$ | — |
| 70 | Ar-14 | 8 | Single bond | —$NR_1C(=O)NR_2$— | H | H | *$C_2H_4OC_{12}H_{25}$ | — |

A compound represented by Formula (1A) may be synthesized by conventional method. For example, it may be synthesized by referring the method described in Jikken Kagaku Koza (5$^{th}$ edition), 26, 160-169 (Maruzen, 2005).

(Compound Represented by Formula (1B))

The organic piezoelectric material of the present invention is characterized in comprising a compound represented by Formula (1B) or a polymer having a residual group of a compound represented by Formula (1B) in a side chain through $Q_1$ or $Q_2$, and a base material comprising a resin.

$$Q_1\text{-}A_1\text{-}(L_1\text{-}A_1)_n\text{-}Q_2, \quad \text{Formula (1B)}$$

In Formula (1B), $Q_1$ and $Q_2$ each independently represents an un-substituted aromatic group, an aromatic group substituted by an alkyl group or an alkoxy group, or a cyclolkyl group substituted by an alkyl group or an alkoxy group. Examples of aromatic group in Q1 or Q2 include phenyl group, naphthyl group or anthranil group; and cycloalkyl group include cyclohexyl group, or cyclopentyl group. Specific examples for alkyl group as substituent of aromatic group or cycloalkyl group include methyl group, ethyl group, propyl group, isopropyl group, tert-butyl group, pentyl group, hexyl group, octyl group, decyl group, octadecyl group, or cyclohexyl group. As for alkyl group as substituent, preferred is an alkyl group having 5-20 carbons, more preferable having 6-15 carbons. Specific examples for alkoxy group include methoxy group, ethoxy group, propyloxy group, pentyloxy group, cyclopentyloxy group, hexyloxy group, octyloxy group, decyloxy group, octadecyloxy group, or cyclohexyloxy group. As for alkoxy group, preferred is an alkoxy group having 5-20 carbons, more preferable having 6-15 carbons.

$A_1$ represents —NR$_1$C(=O)NR$_2$—, —NR$_1$C(=S)NR$_2$—, —OC(=O)O—, —OC(=S)O—, —NHC(=O)O—, —NHC(=S)O—, —NHC(O)—, —NHC(=S)—, —SO$_2$NH—, or —NHSO$_2$NH—. Of these, —NR$_1$C(O)R$_2$—, —NR$_1$C(=S)NR$_2$—, and —NHSO$_2$NH— are preferably employed.

R$_1$ and R$_2$ each independently represents a hydrogen atom or a substituent. Specific examples of substituent in R$_1$ or R$_2$ include: alkyl group such as methyl group, ethyl group, propyl group, isopropyl group, tert-butyl group, pentyl group, hexyl group, octyl group, decyl group, octadecyl group, or cyclohexyl group; and aromatic group such as phenyl group, naphthyl group or anthranil group. As for alkyl group as substituent, preferred is an alkyl group having 1-20 carbons, more preferable having 1-5 carbons.

n represents an integer of 0-100. It is preferable 0-80, more preferable 0-50.

L$_1$ represents a divalent linking group. Specific examples of divalent linking group include alkylene group, alkyleneoxy group, arylene group, and aralkylene group. Alkylene group includes methylene group, ethylene group, n-propylene group, and n-butylene group. Alkyleneoxy group includes ethyleneoxy group, propyleneoxy group, and octyleneoxy group and polyethyleneoxy group. Arylene group includes phenylene group, naphtylene group and biphenylene group. Aralkylene group includes benzylene group and phenetylene group.

Further, these linking groups may form a divalent linking group in combination with a plurality of linking groups.

L$_1$ is preferable a divalent linking group represented by Formula (2).

$$-Ar-L_2-  \quad \text{Formula (2)}$$

In Formula (2), Ar represents arylene group, such as phenylene group, naphtylene group and biphenylene group. L$_2$ represents a divalent linking group or a bond. Specific examples of divalent linking group include ones represented by L$_1$ in Formula (1B).

The present invention preferably includes the following embodiments.

An organic piezoelectric material described in the above mean 1 characterized in that n in Formula (1B) is zero.

An organic piezoelectric material described in the above mean 1 characterized in that n in Formula (1B) is not less than 1, and L$_1$ is represented by Formula (2).

(Polymer)

The polymer related to the present invention which has a residue of the compound represented by Formula (1B) at a side chain through Q$_1$ or Q$_2$ can be prepared by polymerizing the compound having a polymerizable group and the residue of the compound represented by Formula (1B) through Q$_1$ or Q$_2$.

Specific examples of the compound having a polymerizable group for preparing the compound having a residue of the compound represented by Formula (1B) through Q$_1$ or Q$_2$ include compound having double bond such as acrylic acid derivatives, methacrylic acid derivatives, cinnamic acid derivatives, allyl group and vinyl group.

To these compounds, a residue of the compound represented by Formula (1B) through Q$_1$ or Q$_2$ is bonded and the resulting compound is polymerized by using light, polymerization initiator, catalyst, acid or base, whereby the polymer related to the present invention can be prepared.

As a compound having a polymerizable group, it is preferable to employ a compound having acryloyl group, methacryloyl group, or allyl group, and further acryl acid derivatives or methacrylic acid derivatives having acryloyl group or methacryloyl group.

As catalyst for polymerization, for example, employed is benzoin type compound such as benzoin, benzoin methyl ether, benzoin ethyl ether, and benzoin isopropyl ether; carbonyl compound such as benzyl, benzophenone, acetophenone, and Michler ketone; azo compound such as azobisisobutyronitrile, and azobenzoyl; peroxide such as benzoyl peroxide; and mixture of α-diketone and tertiary amine. Further, polymerization by irradiation of radioactive ray may be employed.

Any temperature may be applied as temperature for polymerization, as long as polymerization is not impaired, however preferably −50-250° C., more preferably −50-200° C. Solution polymerization, deposition polymerization or polymerization without solvent may be employed, however, preferred is solution polymerization or polymerization without solvent. As solvent used for polymerization, preferred is a solvent which can dissolve a reactive substrate and a target compound easily. Specific example of solvent includes aliphatic hydrocarbons such as cyclohexane, pentane or hexane; aromatic hydrocarbons such as benzene, toluene, or chlorobenzene; ethers such as THF (tetrahydro furan), diethyl ether, or ethyleneglycol diethyl ether; ketones such as acetone, methyl ethyl ketone, or 4-methyl-2-pentanone; esters such as methyl propionate, ethyl acetate or butyl acetate; and mixture thereof.

Resulting polymer may be isolated and purified or a resulting solution may be coated as it is to form a film. Preferred is to provide a method for isolation and purification by reprecipitation technique. Any method may be applied for purification by reprecipitation, however, preferred is a method in which reaction solution is dropped into poor solvent and polymer is precipitated, or a method in which poor solvent is added into reaction solution and polymer is precipitated. Herein, poor solvent may be any solvent, as long as solvent does not dissolve a polymer compound represented by Formula (1B). Specific examples include aliphatic hydrocarbons such as cyclohexane, pentane or hexane; aromatic hydrocarbons such as benzene, toluene, or chlorobenzene; ethers such as diethyl ether, or ethyleneglycol diethyl ether, esters such as methyl propionate, ethyl acetate or butyl acetate; and alcohols such as methanol, ethanol, or propanol.

Molecular weight of polymer (weight average molecular weight (Mw)) is preferable 5,000-100,000, more preferable 40,000-100,000. The weight average molecular weight (Mw) of polymer is determined by a gel permeation chromatography (GPC) according to the following manner.

Measurement conditions are as follows

Solvent: 30 mM LiBr in N-methylpyrolidone

Apparatus: HLC-8220GPC (produced by Tosoh Corporation)

Columns: TSK gel Super AWM-H×2 (produced by Tosoh Corporation)

Column temperature: 40° C.

Sample concentration: 1.0 g/L

Injection amount: 400

Flow rate: 0.5 ml/minute

Calibration curve: A calibration curve prepared by employing 9 samples of standard polystyrene PS-1 (produced by Polymer Laboratories, Mw=580-560,000) was employed.

Compound represented by Formula (1B) can be synthesized by conventional procedure.

For example, employable are methods described in JP-A No. 2006-16352, Chemische Berichte, 34, 1901, 1945; J. Chem. Soc. 125, 1924, 1704; J. Chem. Soc. 1927, 440; Chem. Eur. J. 1999, 5, No. 3, 1070-1083, and J. Chem. Soc. 2005, 127, 2565-2571.

Listed below are specific examples of compound represented by Formula (1B), polymerizable compounds for preparing polymer having a residue of the compound represented by Formula (1B) at a side chain through $Q_1$ or $Q_2$, or polymer, however the present invention is not limited thereto.

TABLE 4

Formula (1) $Q_1—A_1—(L_1—A_1)n—Q_2$

| No. | $Q_1$ | $A_1$ | $R_1$ | $R_2$ | $L_1$ | n | $Q_2$ |
|---|---|---|---|---|---|---|---|
| 1 | 3,4,5-tri($C_6H_{13}O$)phenyl | $—NR_1C(=O)NR_2—$ | H | H | — | 0 | 3,4,5-tri($C_6H_{13}O$)phenyl |
| 2 | 3,4,5-tri($C_{12}H_{25}O$)phenyl | $—NR_1C(=S)NR_2—$ | H | H | — | 0 | 3,4,5-tri($C_{12}H_{25}O$)phenyl |
| 3 | 3,4,5-tri($C_{18}H_{37}O$)phenyl | $—NHSO_2NH—$ | — | — | 1,3-cyclohexylenedimethylene | 1 | 3,4,5-tri($C_{18}H_{37}O$)phenyl |
| 4 | phenyl | $—SO_2NH—$ | — | — | — | 0 | 3,4,5-tri($C_{18}H_{37}O$)phenyl |
| 5 | 3,5-di($C_{12}H_{25}O$)phenyl | $—NHC(=S)—$ | — | — | — | 0 | 3,5-di($C_{12}H_{25}O$)phenyl |

TABLE 5

| No. | $Q_1$ | $A_1$ | $R_1$ | $R_2$ | $L_1$ | n | $Q_2$ |
|---|---|---|---|---|---|---|---|
| 6 | 3,4-di($C_{12}H_{25}O$)phenyl | $—NHC(=O)—$ | — | — | — | 0 | 3,4,5-tri($C_{18}H_{37}O$)phenyl |

TABLE 5-continued
| No. | Q₁ | A₁ | R₁ | R₂ | L₁ | n | Q₂ |
|---|---|---|---|---|---|---|---|
| 7 | 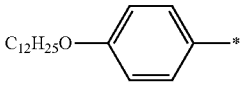 | —NR₁C(=S)NR₂— | H | H | — | 0 | 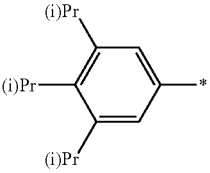 |
| 8 | 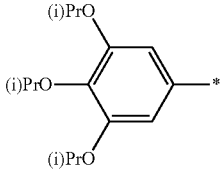 | —OC(=O)O— | — | — | — | 0 | 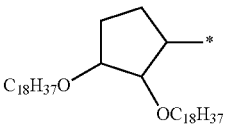 |
| 9 | 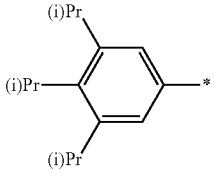 | —NHC(=S)O— | — | — | — | 0 | 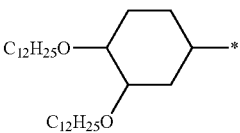 |
| 10 | 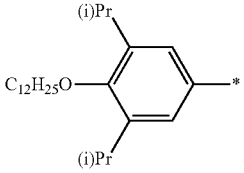 | —NHSO₂NH— | — | — | — | 0 | 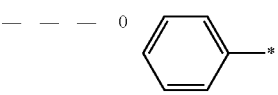 |
TABLE 6
| No. | Q₁ | A₁ | R₁ | R₂ | L₁ | n | Q₂ |
|---|---|---|---|---|---|---|---|
| 11 | 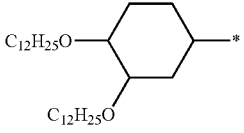 | —OC(=S)O— | — | — | — | 0 | 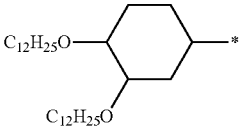 |
| 12 | 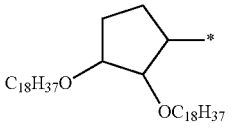 | —NR₁C(=O)NR₂— | H | Me | 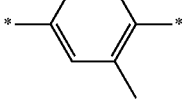 | 1 | 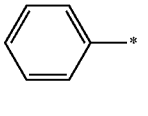 [SMILES: *c1ccccc1] |
| 13 | 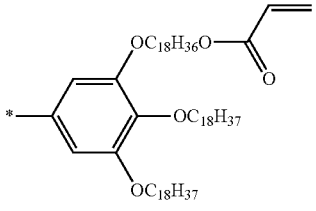 | —NR₁C(=S)NR₂— | H | H | 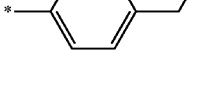 | 1 | 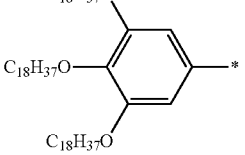 |
| 14 | 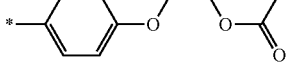 | —SO₂NH— | — | — | 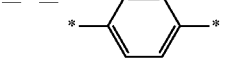 | 1 | 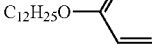 |

TABLE 6-continued

| No. | Q₁ | A₁ | R₁ | R₂ | L₁ | n | Q₂ |
|---|---|---|---|---|---|---|---|
| 15 | C₁₂H₂₅O, C₁₂H₂₅O, C₁₂H₂₅O trisubstituted phenyl | —NR₁C(=S)NR₂— | H | H | para-phenylene | 50 | C₁₂H₂₅O, C₁₂H₂₅O, C₁₂H₂₅O trisubstituted phenyl |

TABLE 7

| No. | Q₁ | A₁ | R₁ | R₂ | L₁ | n | Q₂ |
|---|---|---|---|---|---|---|---|
| 16 | methacrylate-substituted phenyl with C₆H₁₂O, C₆H₁₃, C₆H₁₃ | —NHSO₂NH— | — | — | — | 0 | C₁₂H₂₅O-phenyl-* |
| 17 | Polymer No. 13 | Mw: 20000 | | | | | |
| 18 | Polymer No. 14 | Mw: 30000 | | | | | |
| 19※ | C₈H₁₇O, C₈H₁₇O, C₈H₁₇O trisubstituted phenyl | —NR₁C(=O)NR₂— | H | H | — | 0 | C₈H₁₇O, C₈H₁₇O, C₈H₁₇O trisubstituted phenyl |

※ JP-A No. 2006-016352

(Base Material Comprising Resin)

The organic piezoelectric material of the present invention is characterized by comprising the specific compound (1) and a base material comprising a resin, wherein CLogP(I) and CLogP(base material) satisfies a relation represented by Expression (1), provided that CLogP(1) and CLogP(base material) each represents ClogP of the specific compound (1) and the base material.

$$|CLogP(1A)-CLogP(\text{base material})| \leq 3.0, \quad \text{Expression (1)}$$

When the specific compound (1) is formed to an organic piezoelectric film, it is required to mix further appropriate resin (polymer compound) as a base material for enhancing film forming Property.

As a resin for mixing, a thermoplastic resin, a thermosetting resin or photo curable resin having a number average molecular weight of 1,500 or more are employable.

As a thermoplastic resin, one having a number average molecular weight of 1,500 or more, preferably 1,500-100,000 is employable without limitation. When a number average molecular weight of a thermoplastic resin is 1,500 or less, a glass transition temperature may become too low, whereby may cause low mechanical stability of the organic piezoelectric film.

Specific examples for thermoplastic resin preferably employable to the present invention include halogenated vinyl polymer or copolymer such as polyvinyl chloride, polyvinyl bromide, polyvinyl fluoride, vinyl chloride-vinyl acetate copolymer, vinyl chloride-ethylene copolymer, vinyl chloride-propylene copolymer, vinyl chloride-vinylidene chloride copolymer, vinyl chloride-butadiene copolymer, vinyl chloride-acrylic ester copolymer, vinyl chloride-acrylonitrile copolymer, vinyl chloride-styrene-acrylonitrile terpolymer, vinyl chloride-vinylidene chloride-vinyl acetate copolymer, polyvinylidene chloride, polytetrafluoro ethylene, and polyvinylidene fluoride; polymer or copolymer of unsaturated alcohol or ether such as polyvinyl alcohol, polyaryl alcohol, polyvinyl ether, and polyaryl ether; polymer or copolymer of unsaturated carboxylic acid such as acrylic acid or methacrylic acid; polymer or copolymer of one having unsaturated bond in alcohol residue such as polyvinyl ester such as polyvinyl acetate, or polyaryl ester such as polyphthalic acid; polymer or copolymer having acid residue such as polyacrylate ester, polymethacrylate ester, maleate ester or fumarate ester, or having acid residue and unsaturated bond in alcohol residue; unsaturated nitrile polymer or copolymer such as polymer or copolymer of acrylonitril or methacrylonitril, or polyvinyl cyanide, polymer or copolymer of malononitrile or fumaronitrile; polymer or copolymer of aromatic vinyl compound such as polystyrene, poly α-methyl styrene, poly p-methyl styrene, styrene-α-methyl styrene copolymer, styrene-p-methyl styrene copolymer, polyvinyl benzene, or poly halogenated styrene; polymer or copolymer of heterocyclic compound such as polyvinyl pyridine, poly-N-vinyl pyrrolidine, poy-N-vinyl pyrolidone; polyester condensate such as polycarbonate; polyamide condensate such as nylon 6 or nylon 6,6; polymer or copolymer comprising maleic anhydride, fumaric anhydride or imide compound thereof; and heat-resisting organic polymer such as polyamideimide, polyetherimide, polyphenylene oxide, polyphenylene sulfide, polysulfone, polyether sulfone, or polyarylate. Of these, polycarbonate, polystyrene, polyacrylate, polymethacrylate and nylon are preferably employed.

As thermosetting resins, employable are various species of resins including available in the market such as epoxy type adhesives or acryl type adhesives. As photo curable resins, employable are various species of resins including available in the market such as adhesives curable by visible light, UV light or electron beam. These non-liquid-crystalline polymers may be appropriately selected in view of a production method of an organic piezoelectric film or a required resistance.

Specific examples for thermosetting resin or photo curable resin preferably employable to the present invention include epoxy type adhesives, acryl type adhesives, unsaturated polyester type adhesives, polyurethane type adhesives, hot melt type adhesives, and elastomer type adhesives.

As an example of epoxy type adhesives, bisphenol A type is preferably used as base compound. Bisphenol compound below may be employable as base compound at a portion of bisphenol A.

As an example of polyurethane type adhesives, listed are methylene bis(p-phenylene diisocyanate), tolylene diisocyanate, hexamethylene diisocyanate, 1-chlorophenyl diisocyanate, 1,5-naphthylene diisocyanate, thiodipropyl diisocyanate, ethylbenzene-α-2-di-isocyanate, and 4,4,4-triphenylmethane triisocyanate as an isocyanate component. As a component reacting with above components, listed are ethylene glycol, propylene glycol, triethylene glycol, tetraethylene glycol, glycerol, hexane triol, xylene diol, lauric acid monoglyceride, stearic acid monoglyceride, oleic acid monoglyceride, polyethylene glycol, polypropylene glycol, polyester and polyamide.

Content of mixing above resin compound is 10-80% by mass, preferable 20-80% by mass based on the specific compound (1). When content of the resin compound is less than 10% by mass, it may cause lower performance of film formation or lack of mechanical strength of liquid crystal layer. On the other hand, when content of the resin compound exceeds 80% by mass, it may cause unwanted light scattering, resulting in lowering performance of organic piezoelectric film.

Further, the compound (1) may be used in mixture with other ferroelectric polymer. Specifically, employable are polyvinylidene fluoride (PVDF), vinylidene fluoride/ethylene trifluoride copolymer P (VDF/TrFE), vinylidene fluoride/ethylene tetrafluoride copolymer P (VDF/TeFE), vinylidene cyanide/vinyl acetate copolymer P (VDCN/VA), vinyl fluoride/ethylene trifluoride copolymer P (VF/TrFE), copolymer prepared by adding the third component such as vinylidene fluoride, ethylene tetrafluoride, hexafluoro acetone and hexafluoro propylene to vinyl fluoride/ethylene trifluoride copolymer P (VF/TrFE); or amide type polymer such as nylon 7 or nylon 11, aliphatic polyurea, and aliphatic polyurethane.

(Organic Piezoelectric Material)

The organic piezoelectric material of the present invention may form an organic piezoelectric film by forming film comprising the specific compound (1) and the base material comprising the resin, or further by performing polarization treatment on the resulting film.

When a stress is applied to an organic piezoelectric material film, charges having opposite sign are formed at both end faces of the organic piezoelectric material film in proportion to the stress, which is called as phenomenon of an electric polarization. On the contrary, when the organic piezoelectric material film is set in an electric field (electric field is applied), the organic piezoelectric material film has a property to form a strain in proportion to the electric field (piezoelectric property). Specifically in the organic piezoelectric material film comprising the organic piezoelectric material of the present invention, a large piezoelectric effect can be formed by a polarization due to an orientation freezing of a dipole moment in a polymer main chain or side chain.

Further, when energy (heat) is applied to the organic piezoelectric material film, degree of a spontaneous polarization inside of the organic piezoelectric material film is changed according to the energy. Since a surface charge which exists to neutralize the spontaneous polarization at a surface of the organic piezoelectric material film cannot correspond to an energy change so quickly as above spontaneous polarization, whereby even in short time, there exists a charge at a surface of the organic piezoelectric material film which corresponds to the amount of the changed spontaneous polarization. This generation of electricity according to the energy change is referred to as pyroelectric property. Specifically in the organic piezoelectric material film comprising the organic piezoelectric material of the present invention, a large pyroelectric property can be formed by a polarization due to an orientation freezing of a dipole moment in a polymer main chain or side chain.

(Method for Forming Organic Piezoelectric Material Film)

An organic piezoelectric material film is preferably formed via coating method. As examples for coating method, listed are a spin coating method, a solvent casting method, a melt casting method, a melt press method, a roll coating method, a flow coating method, a printing method, a dip coating method, and a bar coating method.

(Polarization Treatment)

As a polarization treatment method in the polarization treatment in the present invention, there can be applied various well-known methods. For example, in the corona discharge treatment method, the corona discharge treatment can be carried out employing an apparatus available on the market composed of a high voltage power source and an electrode.

It is preferred that discharge conditions are properly selected, since they vary due to kind of an apparatus used or treatment ambience. When the high voltage power source is used, the voltage is preferably from −1 to −20 kV, the current is preferably from 1 to 80 mA, the distance between the electrodes is preferably from 1 to 10 cm, and voltage applied is preferably from 0.5 to 2.0 MV/m. The electrode used is preferably a needle electrode, a linear electrode (wire electrode) or a network electrode, each being conventionally used, but the present invention is not limited thereto.

Further, for heating while a corona discharge, a heater has to be set under the electrode whereto the prepared substrate by the present invention is contacted through an insulator.

It is safe to ventilate adequately to remove volatile components of a solvent in order to avoid fire and explosion hazard, when a corona discharge treatment is employed as a polarization treatment during a solvent of a coating solution being remained.

(Substrate)

The substrate used is selected according to usage of the organic piezoelectric material layer in the present invention. As the substrate in the present invention, there can be used a plate or film of a plastic such as polyimide, polyamide, polyimideamide, polyethylene terephthalate (PET), polyethylene naphthalate (PEN), polymethyl methacrylate (PMMA), a polycarbonate resin, or a cycloolefin polymer. The substrate may be those in which the surface of these materials is covered with aluminum, gold, copper, magnesium, or silicon. The substrate may be a plate or a film of simple substance of aluminum, gold, copper, magnesium, silicon or a single crystal of a halide of rare earth element.

Further, an organic piezoelectric material layer may be formed onto multilayer piezoelectric elements. As for a multilayer obtained by laminating piezoelectric elements, there is a method of laminating the organic piezoelectric material film of the present invention via an electrode on a ceramic piezoelectric element. As the ceramic piezoelectric element, PZT is frequently employed, but it has recently been recommended to employ one containing no lead.

PZT represented by $Pb(Zr_{1-x}Ti_x)O_3$ is preferable within the range of $0.47 \leq x \leq 1$, but examples of the material containing no lead include a natural or synthetic quartz, lithium niobate ($LiNbO_3$), potassium niobate tantalate [$K(Ta, Nb)O_3$], barium titanate ($BaTiO_3$), lithium tantalite ($LiTaO_3$), strontium titanate ($srTiO_3$) and so forth. Compositions of various ceramic materials can be selected appropriately for performance in use.

(Ultrasound Transducer)

An ultrasound transducer according to the present invention is characterized by using an organic piezoelectric film formed by using the organic piezoelectric material of the present invention. The ultrasound transducer is preferably allowed to be an ultrasound receiving transducer used in an ultrasound medical diagnostic imaging device probe provided with an ultrasound transmitting transducer and an ultrasound transmitting transducer.

Incidentally, an ultrasound transducer is usually constituted by arranging a pair of electrodes so as to sandwich a layer (or a film) formed of a film-shaped piezoelectric material (also referred to as a "piezoelectric film," a "piezoelectric material film," or a "piezoelectric body layer"), and then an ultrasound probe is constituted, for example, via one-dimensional arrangement of a plurality of such transducers.

A predetermined number of such transducers of the long axis direction arranged with a plurality of the transducers are set as an aperture, and thereby a function is performed in which a plurality of the transducers belonging to the aperture are driven; an ultrasound beam is focused on and irradiated to a measurement portion in a tested subject; and also an ultrasound reflective echo emitted from the tested subject is received by a plurality of the transducers belonging to the aperture for conversion into an electrical signal.

FIG. 1 is an example of an embodiment showing the basic construction of an ultrasound transducer. In ultrasound transducer 10, electrodes 2 are arranged at both side of piezoelectric material 1. Electrodes 2 may be arranged properly on all over or on a partial portion of organic piezoelectric material 1.

An ultrasound receiving transducer and an ultrasound transmitting transducer according to the present invention will now be detailed.

<Ultrasound Receiving Transducer>

An ultrasound receiving transducer according to the present invention is a transducer having an ultrasound receiving piezoelectric material used for a probe of an ultrasound medical diagnostic imaging device. A piezoelectric material constituting the transducer is preferably an embodiment employing an organic piezoelectric film formed using the organic piezoelectric material of the present invention.

Herein, an organic piezoelectric material or an organic piezoelectric film used in an ultrasound receiving transducer preferably has a specific dielectric constant of 10-50 in the thickness resonance frequency. Adjustment of the specific dielectric constant can be carried out via adjustment of the number of the above substituent R possessed by a compound constituting the organic piezoelectric material or a polar functional group such as a $CF_2$ group or CN group, the composition, and the degree of polymerization, as well as via the above polarization treatment.

Further, an organic piezoelectric material film constituting the receiving transducer of the present invention can be constituted by laminating a plurality of polymer materials. In this case, as such laminated polymer materials, other than the above polymer materials, the following polymer materials having relatively small specific dielectric constant can be combined.

Herein, in the following examples, each number in a parenthesis represents the specific dielectric constant of a polymer material (resin).

For example, usable is methyl methacrylate resin (3.0), acrylonitrile resin (4.0), acetate resin (3.4), aniline resin (3.5), aniline formaldehyde resin (4.0), aminoalkyl resin (4.0), alkyd resin (5.0), nylon-6-6 (3.4), an ethylene resin (2.2), epoxy resin (2.5), vinyl chloride resin (3.3), vinylidene chloride resin (3.0), urea formaldehyde resin (7.0), polyacetal resin (3.6), polyurethane (5.0), polyester resin (2.8), polyethylene (low-pressure) (2.3), polyethylene terephthalate (2.9), a polycarbonate resin (2.9), a melamine resin (5.1), melamine formaldehyde resin (8.0), cellulose acetate (3.2), vinyl acetate resin (2.7), styrene resin (2.3), styrene butadiene rubber (3.0), styrol resin (2.4), or ethylene fluoride resin (2.0).

Herein, the polymer materials having relatively small specific dielectric constant are preferably selected depending on the intended purposes to adjust piezoelectric characteristics or to provide physical strength for an organic piezoelectric material film.

<Ultrasound Transmitting Transducer>

An ultrasound transmitting transducer according to the present invention is preferably constituted of a piezoelectric material having an appropriate specific dielectric constant in view of the relationship with a transducer incorporating the above receiving piezoelectric material. Further, a piezoelectric material exhibiting excellent heat resistance and voltage resistance is preferably used.

As an ultrasound transmitting transducer constituent material, various well-known organic piezoelectric materials and inorganic piezoelectric materials can be used.

As such an organic piezoelectric material, a polymer material similar to the above ultrasound receiving transducer constituent organic piezoelectric material can be used.

As such an inorganic material, usable is crystal, lithium niobate ($LiNbO_3$), potassium niobate tantalate [$K(Ta, Nb)O_3$], barium titanate ($BaTiO_3$), lithium tantalate ($LiTaO_3$), lead titanate zirconate (PZT), strontium titanate ($SrTiO_3$), or barium strontium titanate (BST). Herein, PZT is preferably $Pb(Zr_{1-n}Ti_n)O_3$ ($0.47 \leq n \leq 1$).

<Electrode>

A piezoelectric (material) transducer according to the present invention is produced in such a manner that an electrode is formed on both sides or one side of a piezoelectric material film (layer) and the piezoelectric material film is polarized. When an ultrasound receiving transducer employing an organic piezoelectric material is produced, the above first surface electrode having been used in polarization treatment can be used as such. The electrode is formed using an electrode material mainly containing gold (Au), platinum (Pt), silver (Ag), palladium (Pd), copper (Cu), nickel (Ni), or tin (Sn).

In formation of an electrode, initially, a base metal such as titanium (Ti) or chromium (Cr) is formed into a thickness of 0.02-1.0 μm by a sputtering method, and thereafter a metal mainly containing the above metal element and a metal material containing an alloy thereof, as well as partially an insulating material if appropriate are formed into a thickness of 1-10 μm by using a sputtering method, a deposition method, or another appropriate method. Such electrode formation can be carried out, other than the sputtering method, via screen printing, a dipping method, or a spraying method using an electrically conductive paste prepared by mixing fine-powdered metal powder with low-boiling point glass.

Further, a predetermined voltage is supplied between the electrodes formed on both sides of a piezoelectric material film and thereby the piezoelectric material film is polarized to obtain a piezoelectric element.

(Ultrasound Probe)

An ultrasound probe according to the present invention is a main component part of an ultrasound medical diagnostic imaging system, which has functions of transmission and reception of ultrasound beam as well as emitting ultrasound. Inside of the ultrasound probe may be constituted in various embodiments. As general constitution, the probe may comprise a tip section (face contacting to living body test object), provided thereon "acoustic lens", "acoustic matching layer", "ultrasound transducer (element)", and "backing layer" in these order.

An ultrasound probe according to the present invention is an ultrasound medical diagnostic imaging device probe provided with an ultrasound transmitting transducer and an ultrasound receiving transducer, and has such a feature that the ultrasound receiving transducer of the present invention is used as a receiving transducer.

In the present invention, only a single transducer may play a role for both transmission and reception of ultrasounds. However, more preferably, transducers for transmission and reception are separately constituted in a probe.

As a piezoelectric material constituting a receiving transducer, a well-known ceramics inorganic piezoelectric material or organic piezoelectric material can be used.

In an ultrasound probe according to the present invention, the ultrasound receiving transducer of the present invention can be arranged on or in parallel to a transmitting transducer.

As a more preferred embodiment, a constitution is preferable in which the ultrasound receiving transducer of the present invention is laminated on an ultrasound transmitting transducer. In this case, the ultrasound receiving transducer of the present invention may be laminated on a transmitting transducer via attachment on another polymer material (the above polymer (resin) film of relatively small specific dielectric constant serving as a support, for example, polyester film). In such a case, the thickness of the receiving transducer and such another polymer material in total preferably corresponds to a preferable receiving frequency band from the viewpoint of probe designing. In view of a practical ultrasound medical diagnostic imaging device and an actual frequency band for living body information gathering, the thickness is preferably 40-150 μm.

Incidentally, a backing layer, an acoustic matching layer, and an acoustic lens may be arranged for the probe. Further, a probe may be formed in which transducers having a large number of piezoelectric materials are arranged two-dimensionally. A constitution as a scanner may be employed to sequentially scan a plurality of two-dimensionally-arranged probes for imaging.

Figure 2:
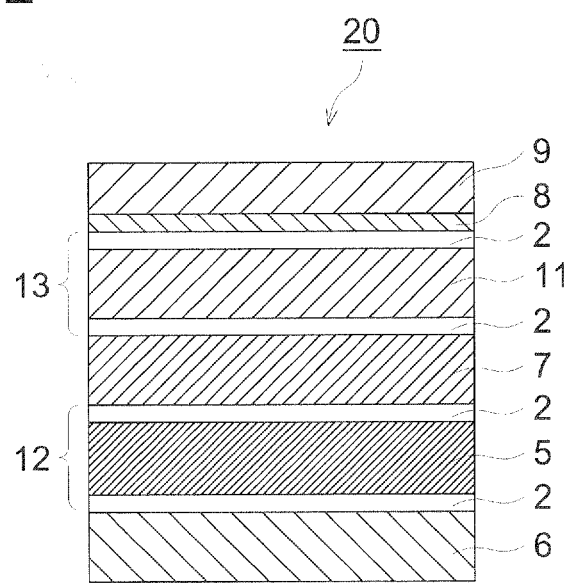
FIG. 2 is a schematic cross-sectional view showing the basic construction of an ultrasound probe.

FIG. 2 is an example showing the fundamental constitution of an ultrasound probe. An ultrasound probe 20 has a construction which comprises backing layer 6, provided thereon ultrasound transmitting transducer 12, substrate 7, ultrasound receiving transducer 13, acoustic matching layer 8 and acoustic lens 9, in these order, wherein ultrasound transmitting transducer 12 has electrodes 2 on the both side of ultrasound transmitting material 5, and ultrasound receiving transducer 13 has electrodes 2 on the both side of ultrasound receiving material 11.

(Acoustic Matching Layer)

Since a difference between acoustic impedances of ultrasound transducer and living tissue is large, large reflection occurs at boundary and results in lasting free-vibration. So as to compensating this influence, an acoustic matching layer having an intermediate acoustic impedance is provided between a transducer and a living tissue, thereby the reflection is reduced, the free-vibration is rapidly terminated, and pulse width of ultrasound transmitted and received by the probe becomes shorter, resulting that ultrasound can effectively transmit into a living body.

As materials for acoustic matching layer, employable are aluminum, aluminum alloy (for example, Al—Mg alloy), magnesium alloy, Macor glass, glass, fused quartz, carbon graphite, copper graphite, polyethylene (PE), polypropylene (PP), polycarbonate (PC), ABC resin, polyphenylene ether (PPE), ABS resin, AAS resin, AES resin, nylon (PM, PA6-6), PPO (polyphenylene oxide), PPS (polyphenylene sulfide: also applicable with glass fiber), PEEK (polyether ether keton), PAI (polyamide imide), PETP (polyethylene terephthalate), epoxy resin and urethane resin. It is preferable to employ a molded material comprising a thermosetting resin such as epoxy resin by adding filler such as zinc flower, titan oxide, silica, alumina, colcothar, ferrite, tungsten oxide, ytterbium oxide, barium sulfate, tungsten, and molybdenum.

Acoustic matching layer may be constituted in a single layer or a plurality of layers, preferable in 2 or more layers. Thickness of acoustic matching layer has to be determined to satisfy to be $\lambda/4$, provided that a wave length of ultrasound is $\lambda$. In the case of not satisfying it, a plurality of unnecessary spurious appears at a frequency point other than an original resonance frequency and causes a large deviation from fundamental acoustic properties. As the result, reverberation time increases and waveform distortion of reflection echo causes decrease of sensitivity or S/N, resulting in being undesirable. Thus, total thickness of acoustic matching layer is about in a range of 30-500 μm.

(Backing Layer)

In an ultrasound probe, for the purpose of inhibiting propagation of ultrasound to the rear side, it is preferable to provide backing layer which is arranged on the back side of the ultrasound transducer. As the result, pulse width can be shortened. Backing layer supports piezoelectric element and is an ultrasound absorber which can absorb unnecessary ultrasound. As backing material for backing layer, employable are press-molded materials in which powder such as titan oxide or ferrite is filled into natural rubber, ferrite rubber, or epoxy resin; thermoplastic resin such as vinyl chloride, polyvinyl butyral (PVB), ABS resin, polyurethane (PUR), polyvinyl alcohol (PVAL), polyethylene (PE), polypropylene (PP), polyacetal (POM), polyethylene terephthalate (PETP), fluorine resin (PTFE), polyethylene glycol, and polyethylene terephthalate-polyethylene glycol copolymer.

Rubber type composite material and/or epoxy type composite material is used for preferable backing material. Shape thereof may be selected appropriately according to a shape of a piezoelectric material or a probe head having piezoelectric material.

As rubber type composite material, it is preferable to contain a rubber component and filler, and has hardness of from A70 by type A Durometer to D70 by type D Durometer determined by Spring hardness tester (Durometer hardness) based on JIS K6253. Further, various kinds of other compoundings may be added, if necessary. As rubber component, preferred are ethylene propylene rubber (EPDM or EPM), hydrogenated nitrile rubber (HNBR), chloroprene rubber (CR), silicone rubber, blended rubber of EPDM and HNBR, blended rubber of EPDM and nitrile rubber (NBR), blended rubber of NBR and/or HNBR and high styrene rubber (HSR), and blended rubber of EPDM and HSR. More preferred are ethylene propylene rubber (EPDM or EPM), hydrogenated nitrile rubber (HNBR), blended rubber of EPDM and HNBR, blended rubber of EPDM and nitrile rubber (NBR), blended rubber of NBR and/or HNBR and high styrene rubber (HSR), and blended rubber of EPDM and HSR. As rubber component of the present invention, a kind of rubber component such as vulcanized rubber or thermoplastic elastomer may be singly used, or blended rubber in which 2 or more kind of rubbers are mixed may also be used. As filler added to rubber component, various type as well as content thereof may be selected from conventional type to one having high specific gravity. For example, listed are metal oxide such as zinc flower, titanium white, colcothar, ferrite, alumina, tungsten trioxide, and ytterbium oxide; clay such as calcium carbonate, hard clay, and diatomite; glass powder or various metal fine powders such as tungsten or molybdenum; and various balloon such as glass balloon or polymer balloon. These fillers may be added in various contents, but preferably 50-3,000 parts by mass based on 100 parts of rubber component, more preferably 100-2,000 parts by mass or 300-1,500 parts by mass. Further, these fillers may be added individually or in combinations of at least 2 types.

Other compounding may be further incorporated appropriately to a rubber complex material. These compounding include vulcanizing agent, cross-linking agent, hardening agent, and auxiliaries thereof, anti-deterioration agent, antioxidant and colorants. For example, carbon black, silicone dioxide, process oil, sulfur (vulcanizing agent), dicumyl peroxide (Dicup, cross-linking agent), and stearic acid may be incorporated. These compounding may be used as appropriate. A used amount thereof is generally about 1-100 parts by mass based on 100 parts of rubber component, but it may be appropriately changed for total balance or characteristics.

Epoxy resin complex material preferably comprises epoxy resin component and filler. Other compounding may be further incorporated appropriately. Specific examples of epoxy resin component includes novolac type epoxy resin such as bisphenol A type, bisphenol F type, resol novolac type, and phenol modified novolac type; multi-cyclic aromatic type epoxy resin such as type containing naphthalene structure, type containing anthracene structure and type containing fluorene structure; hydrogenated alicyclic epoxy resin and liquid-crystal type epoxy resin. These epoxy resin components may be used individually or in combinations of at least 2 types such as blend resin.

As filler added to epoxy component, each of from the same one as the filler mixed in the above rubber component to a complex particles prepared by pulverizing above rubber type complex material may be preferably employable. For example, complex particles include particles having particle size of about 200 μm which are prepared by filling ferrite in silicone rubber and pulverizing by a pulverizer.

When using epoxy resin complex material, further cross-linking agent has to be added. For example, listed are linear aliphatic polyamine such as methylene triamine, triethylene tetramine, dipropylene diamine, and diethylamino propyl amine; cyclic aliphatic polyamine such as N-aminoethyl pyperadine, mensen diamine, and isophorone diamine; aromatic amine such as m-xylene diamine, metaphenylene diamine, diamino diphenyl methane, and diamino diphenyl sulfon; secondary and tertiary amine such as polyamide resin, pyperidine, N,N-dimethyl pyperadine, triethylene diamine, 2,4,6-tris(dimethyl amino methyl)phenol, benzyl dimethyl amine, and 2-(dimethyl amino methyl)phenol; imidazoles such as 2-methyl imidazole, 2-ethyl imidazole, and 1-cyanoethyl-2-undecyl imidazolium trimeritate; liquid polymercaptan, polysulfide, acid anhydride such as phthalic anhydride, trimellitic anhydride, methyl tetrahydro phthalic anhydride, methyl and methylene tetrahydro phthalic anhydride, methyl butenyl tetrahydro phthalic anhydride, and methyl hexahydro phthalic acid.

Thickness of backing layer is preferable about 1-10 mm, specifically 1-5 mm.

(Acoustic Lens)

The acoustic lens related to the present invention is arranged to focus the ultrasound beam in terms of reflection, resulting in enhance resolution. The present invention is characterized by incorporating a light-emitting material which emits light by irradiating an exciting light in a region of the acoustic lens near to surface of test object.

It is essentially required that the acoustic lens matches to acoustic impedance (density×sound velocity: ($1.4 \times 10^6$-$1.6 \times 10^6$ kg/m$^2$·sec)) of living body by adhering well to the living body and reduces reflection of ultrasound, as well as focusing the ultrasound, and also has small loss of ultrasound as itself.

Namely, the acoustic lens is provided on the portion where it contacts to the body for focusing acoustic wave beam, which is made based on polymeric materials such as conventional rubber. The material for the lens is expected to have enough smaller sound velocity than that of human body, small acoustic attenuation and acoustic impedance close to that of skin in human living body. When lens material has enough smaller sound velocity than that of human body, the lens may be formed convex shape, whereby it slips smoothly and in safety in case of making diagnosis. Small acoustic attenuation results in transmission and reception of ultrasound in high sensitivity. Further, the acoustic impedance close to that of skin in human living body minimizes reflection, namely makes larger transmittance, resulting in transmission and reception of ultrasound in high sensitivity as well.

As materials constituting the acoustic lens of the present invention, employable is conventional homopolymer such as silicone rubber, fluorine silicone rubber, or epichlorohydrin rubber, copolymer rubber such as ethylene-propylene copolymer rubber which is prepared by copolymerizing ethylene and propylene. Of these, silicone based rubber is preferably employed.

As silicone based rubber employable to the present invention, listed is silicone rubber or fluorine silicone rubber. Of these, silicone rubber is preferable in view of characteristic for lens material. Silicone rubber is referred to as organopolysiloxane which has molecular skeleton comprising Si—O bonds and a plurality of organic groups are mainly bonded to these Si atoms. Generally, main component thereof is methyl polysiloxane, where methyl group is 90% or more based on total organic groups. Ones in which hydrogen atom, phenyl group, vinyl group or aryl group is introduced instead of methyl group are also employable. The silicone rubber can be obtained by kneading organo polysiloxane having high polymerization degree with hardner (vulcanizing agent) such as benzoyl peroxide, and by heating to vulcanize and harden. Organic or inorganic filler such as silica and nylon powder and auxiliaries of vulcanization such as sulfur or zinc oxide may be added as appropriate.

Butadiene based rubbers include butadiene singly or copolymer rubbers having butadiene as main component and small amount of styrene or acrylonitril copolymerized thereto. Of these, butadiene rubber is preferable in view of characteristic for lens material. Butadiene rubber is referred to as synthesized rubber by polymerizing butadiene having conjugated double bond. Butadiene rubber can be prepared by polymerizing butadiene singly having conjugated double bond via 1,4- or 1,2-polymerization. Butadiene rubber vulcanized by sulfur or the like may be employable.

Also employable for the acoustic lens is one which is obtained by blending silicone based rubber and butadiene based rubber and by vulcanizing to hardened. For example, above rubber can be obtained by kneading silicone and butadiene in appropriate ratio by using kneading roll, followed by adding vulcanizing agent such as benzoyl peroxide, and by heating to vulcanize and harden. In this case, it is preferable to add zinc oxide as auxiliaries of vulcanization. Zinc oxide promotes vulcanization without deteriorating lens characteristics, resulting in shortening vulcanization time. Other than above, other additives may be added to the extent that the characteristics of colorant or acoustic lens are not impaired. In order to obtain one in which acoustic impedance is approximate to that of human body and sound velocity is smaller than human body and low attenuation, mixing ratio of silicone based rubber and butadiene based rubber is generally preferable 1:1, however this mixing ratio may be changeable as appropriate. Silicone rubbers are available on the market. Specific examples include KE742U, KE752U, KE931U, KE941U, KE951U, KE961U, KE850U, KE555U, and KE575U, all produced by Shin-Etsu Chemical Co., Ltd.; TSE221-3U, TE221-4U, TSE2233U, Xe20-523-4U, TSE27-4U, TSE260-3U, and TSE260-4U, all produced by Momentive Performance Material; SH35U, SH55UA, SH831U, SE6749U, SE1120U, and SE4704U, all produced by Dow Corning Toray.

In the present invention, according to the purpose such as adjusting sound velocity or density, inorganic filler such as silica, alumina, titan oxide or organic resin such as nylon can be incorporated in the base (main component) comprising rubber material such as silicone based rubber described above.

(Ultrasound Medical Diagnostic Imaging System)

Figure 3:
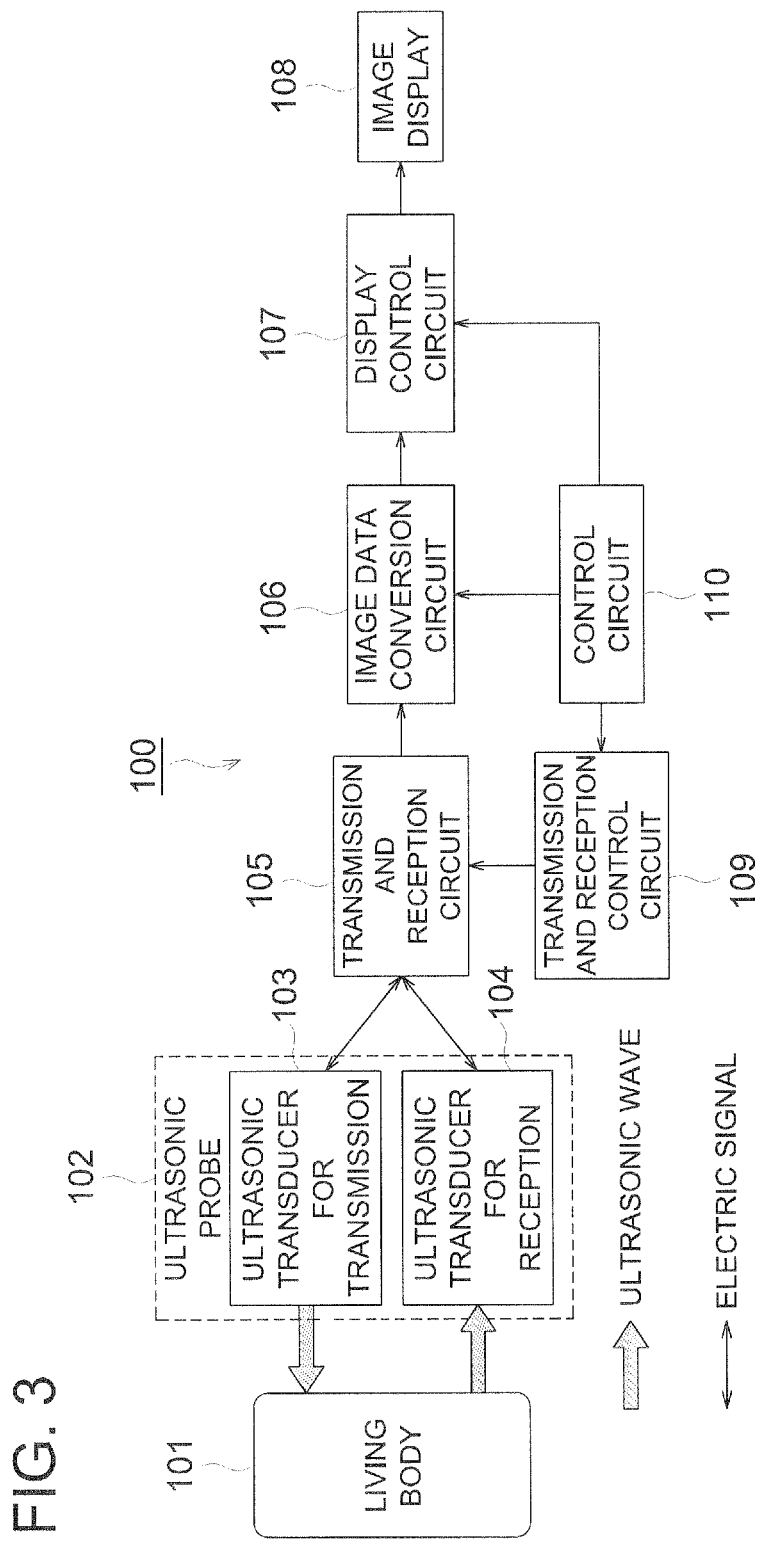
FIG. 3 is a schematic drawing showing the structure of the main section of an ultrasound medical diagnostic imaging system.

The above ultrasound probe of the present invention can be applied to various embodiments of ultrasound diagnostic systems. FIG. 3 shows a schematic drawing of the structure of the main section of an ultrasound medical diagnostic imaging system.

The ultrasound medical diagnostic imaging system is equipped with an ultrasound probe (probe) in which a piezoelectric material transducer is arranged which transmits an ultrasound to an examinee such as a patient and receives an ultrasound reflected from the examinee as an echo signal. Further, the ultrasound medical diagnostic imaging system is equipped with a transmission and reception circuit, which supplies an electric signal to the ultrasound probe to generate ultrasound and receives an echo signal which each piezoelectric material transducer in the ultrasound probe receives, and a transmission and reception control circuit, which controls transmission and reception of the transmission and reception circuit.

The system is further equipped with an image data conversion circuit which converts an echo signal which the transmission and reception circuit receives to an ultrasound image data of an examinee. The system is equipped with a display control circuit, which controls a monitor with an ultrasound image data converted by the image data conversion circuit and displays an image, and a control circuit which controls the entire ultrasound medical diagnostic imaging system.

The transmission and reception control circuit, the image data conversion circuit and the display control circuit are connected to the control circuit and the operation thereof is controlled through the control circuit. An electric signal is applied to each piezoelectric transducer in the ultrasound probe to transmit an ultrasound to an examinee and a reflection wave generated by acoustic impedance mismatch inside the examinee is received by the ultrasound probe.

The ultrasound diagnostic system as described above, comprising the transducer for ultrasound reception of the present invention which is excellent in piezoelectric characteristic and thermal resistance and is suitable for high frequency and broad band, can provide an ultrasound image with improved image quality and reproduction stability as compared with a conventional one.

EXAMPLES

The present invention will now be specifically described with the reference to examples, however the present invention is not limited thereto.

Hereinafter, cases (I) and (II) will be described separately as follows: (I) the case in which the specific compound (1) is a compound having a substructure represented by Formula (1A), and (II) the case in which the specific compound (1) is a compound comprising a compound represented by Formula (1B) or a polymer having a residual group of the compound represented by Formula (1B) in a side chain through $Q_1$ or $Q_2$.

(I): the case in which the specific compound (1) is a compound having a substructure represented by Formula (1A)

Synthesizing Example 1

Synthesis of Compound 18

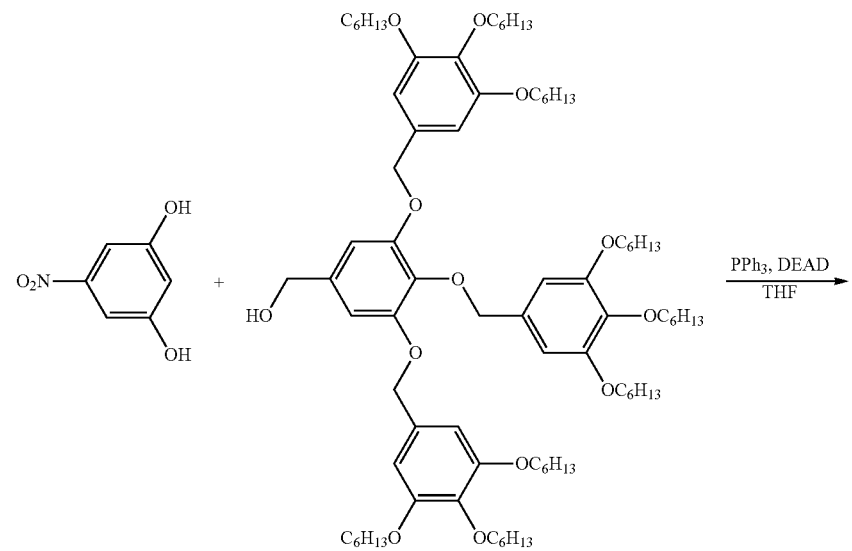

-continued
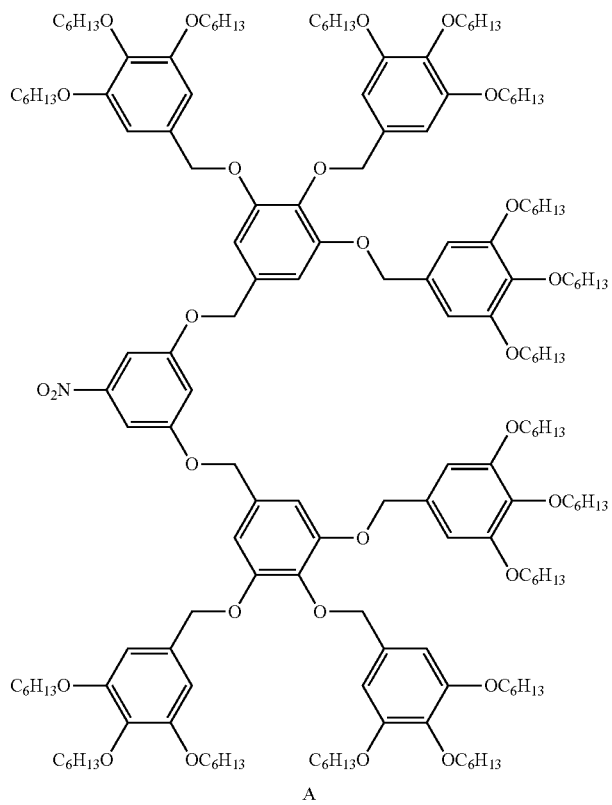
A
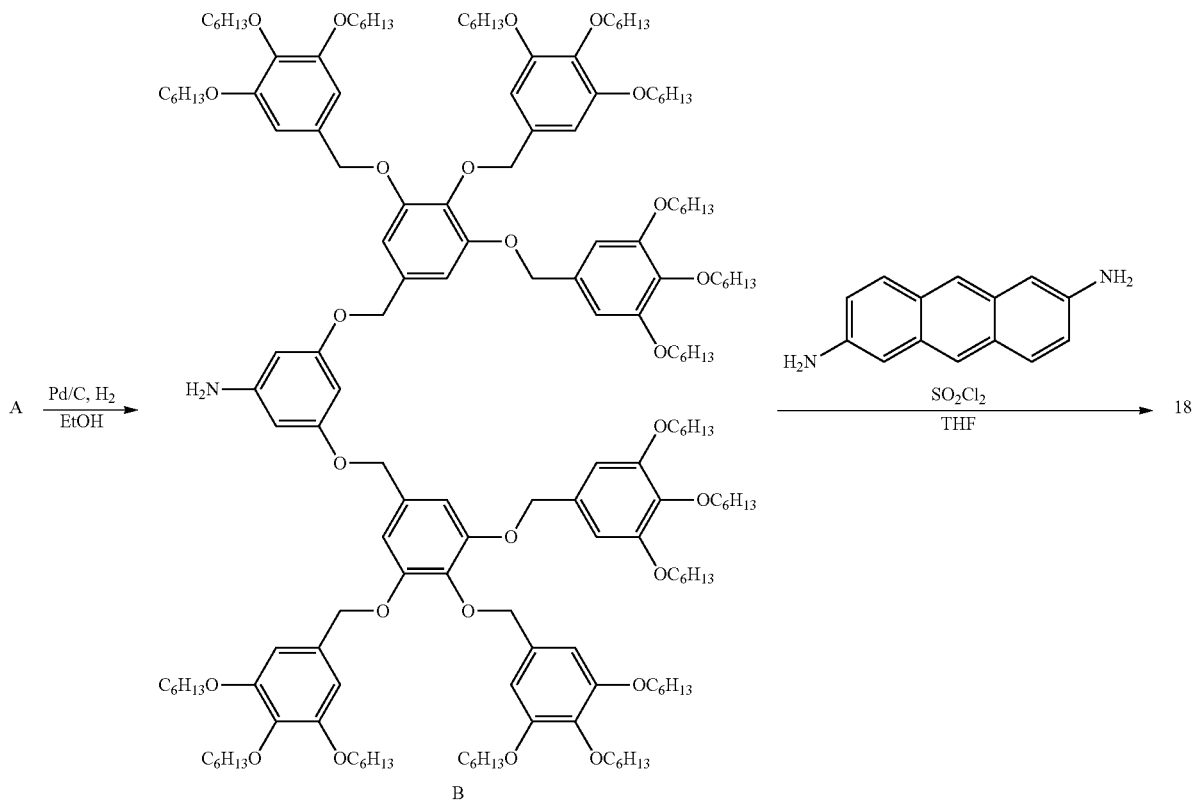

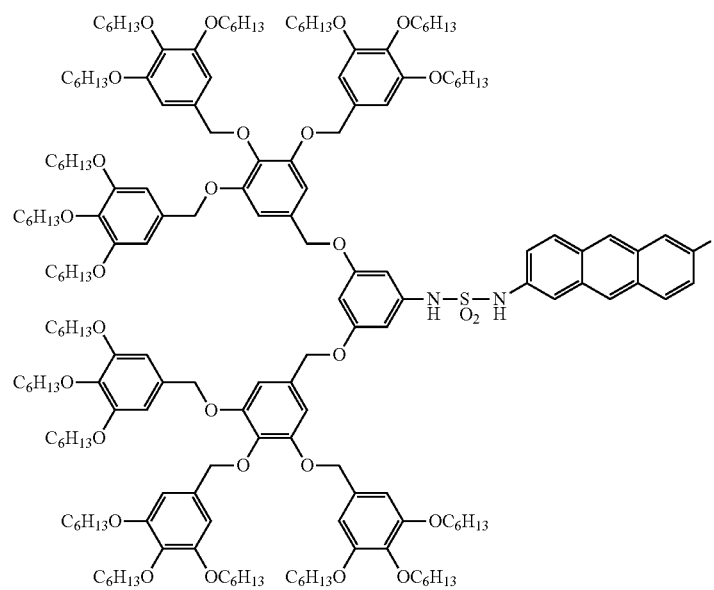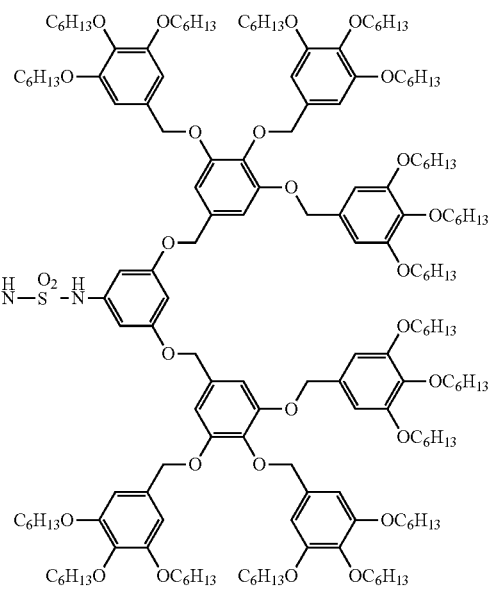

18

(i) Synthesis of Intermediate A

Into a reaction container replaced by nitrogen gas, were loaded 1.5 g of 2,5-dihydroxy-1-nitrobenzene, 26.5 g of 3,4,5-tris[3,4,5-tri(1-hexyloxy)benzyloxy]benzyl alcohol, and 7.9 g of triphenyl phosphine dissolved in 200 ml of dehydrated tetrahydrofuran (THF), and 15 ml of 2.2 M toluene solution of diethyl azocarboxylate (DEAD) was dropped for 30 minutes. After resulting solution was stirred for 5 hours at room temperature, solvent was distilled away under reduced pressure and added was 50 ml of methylethyl ketone. Methanol 100 ml was added to the resulting solution, and precipitated solid was filtered off. After purifying via silica gel chromatography (heptane:ethyl acetate=8:1) to obtain 14.7 g of Intermediate A (yield: 53%).

(ii) Synthesis of Intermediate B

Intermediate A 14.7 g was added to 200 ml of ethanol and replaced by nitrogen gas. After adding 1.0 g of palladium carbon, replaced by hydrogen gas and stirred for 6 hours at room temperature. After palladium carbon was filtered off, ethanol was distilled away under reduced pressure. Resulting solid was recrystallized from methylethyl ketone to obtain 13.9 g of Intermediate B (yield: 96%).

(iii) Synthesis of Compound 18

Into a 1 L of flask, were loaded 200 ml of acetone, 1.5 g (11 mmol) of sulfuryl chloride, and 2.5 g (25 mmol) of triethyl amine to be uniform solution. Under cooling via ice, mixture of 13.9 g (5 mmol) of Intermediate B and 0.5 g (2.5 mmol) of 2,6-diaminoanthracene was dropped for 2 hours. Thereafter, resulting solution was stirred for 24 hours at room temperature, and then 400 g of ice-cold water was added and followed by further stirring overnight. Extraction via methylene chloride was carried out and organic phase was washed by dilute hydrogen chloride. Then, resulting organic phase was dried by sodium sulfate. Resulting solid was purified via silica gel chromatography (toluene:methylene chloride=5:1) to obtain 11.9 g of Compound 18 (yield: 41%). Product was identified by $^1$H-NMR spectra.

$^1$H-NMR spectra (CDCl$_3$, ppm): 0.88 (m. 108H), 1.26-1.41 (m. 216H), 1.76 (m, 72H), 4.06 (m, 72H), 5.10-5.18 (m, 32H), 5.74 (s, 6H), 6.59 (s, 32H), 6.92 (m, 2H), 6.99 (m, 2H), 7.55-8.00 (m, 4H)

Synthesizing Example 2
Synthesis of Compound 26
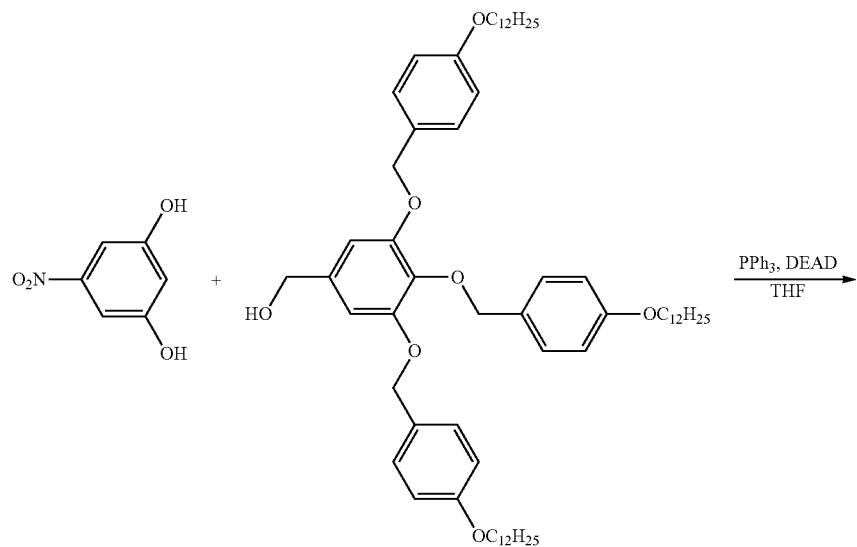
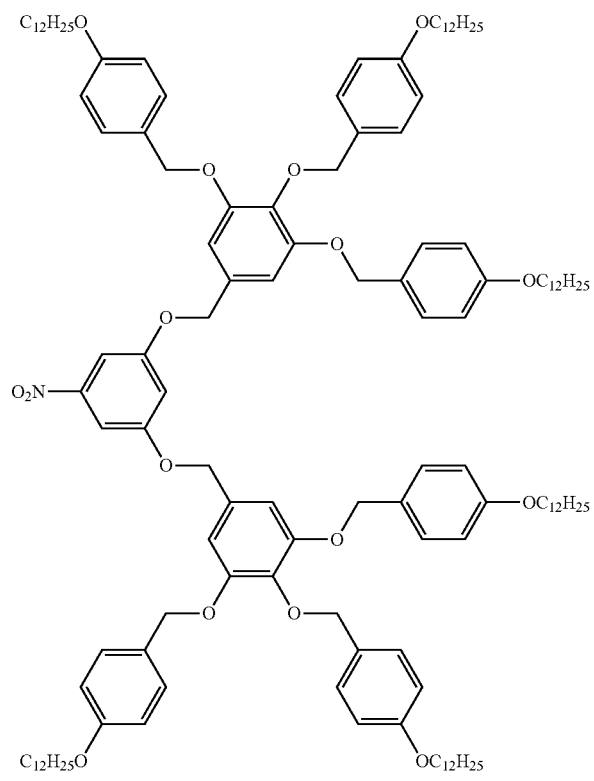
A

-continued
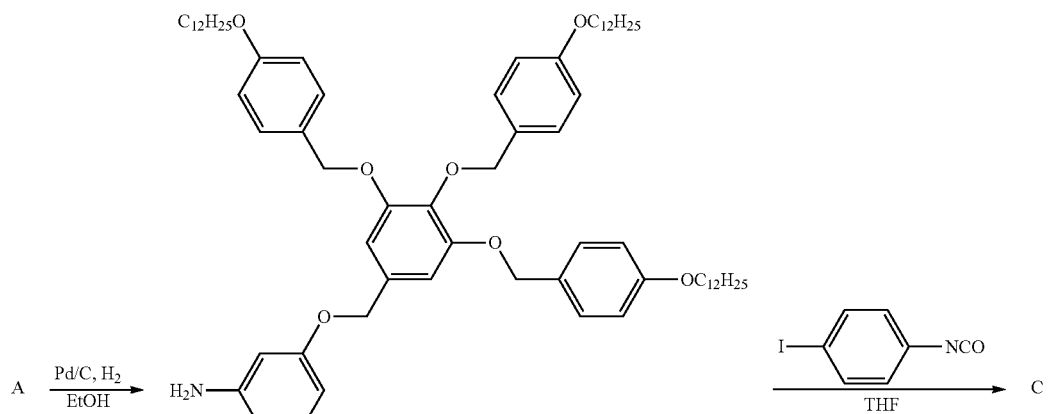
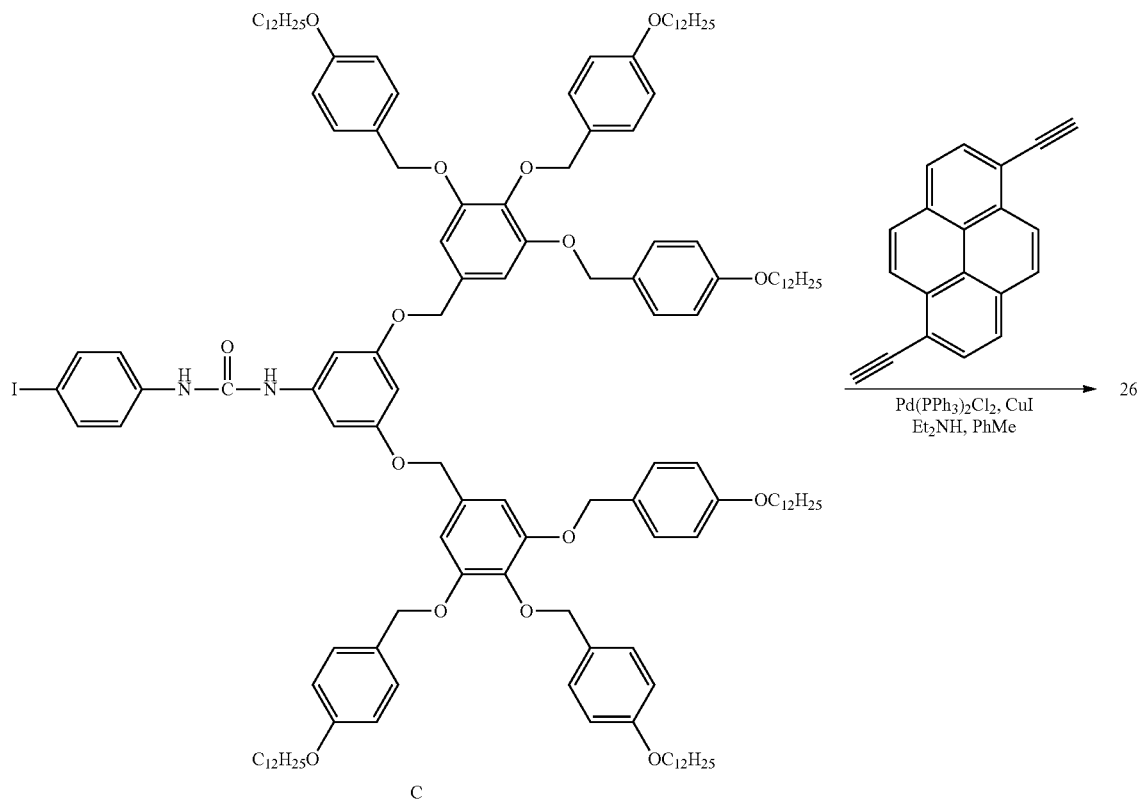

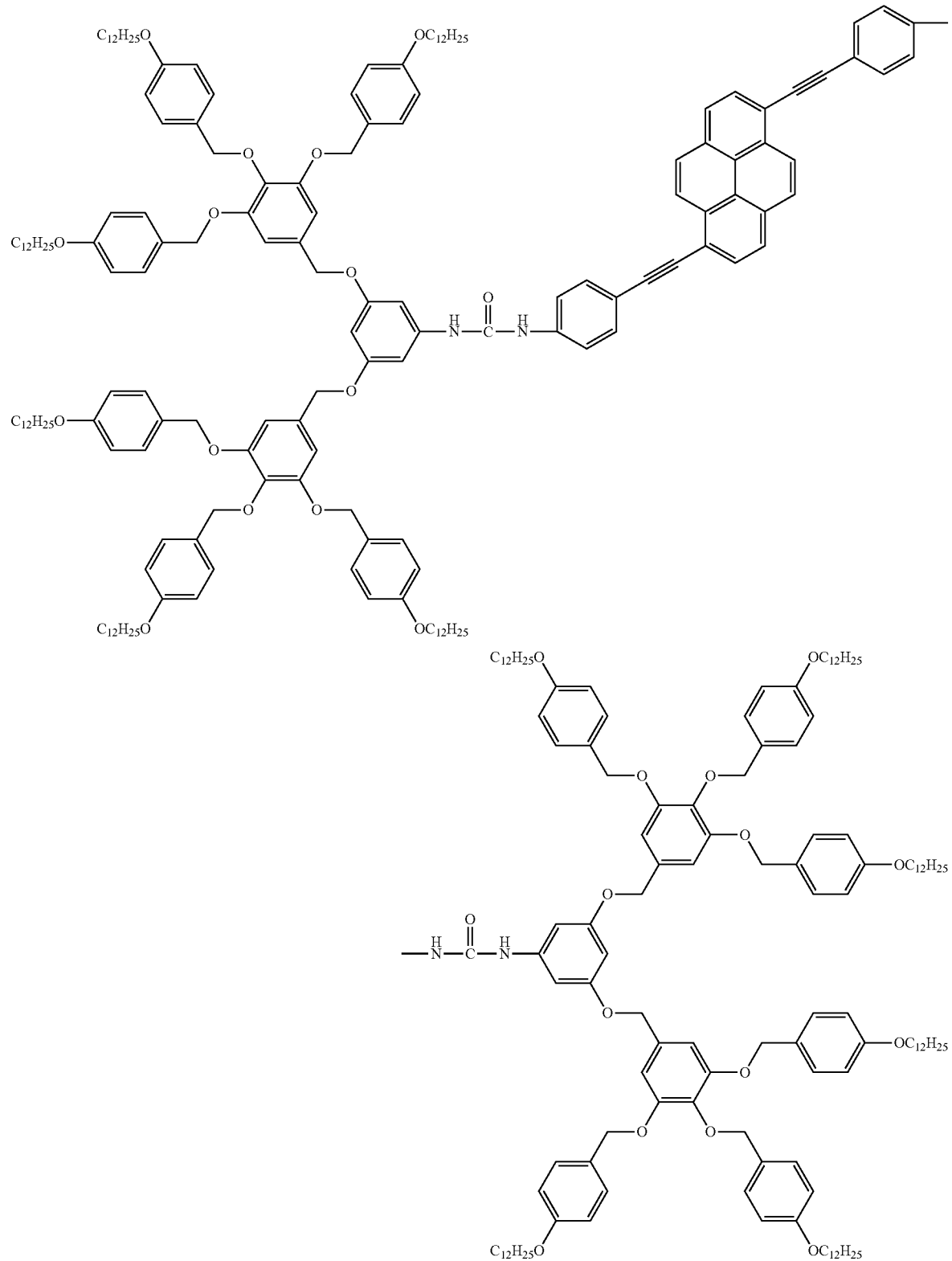

(i) Synthesis of Intermediate A

Into a reaction container replaced by nitrogen gas, were loaded 1.5 g of 2,5-dihydroxy-1-nitrobenzene, 20.0 g of 3,4,5-tris[p-(1-dehexyloxy)benzyloxy]benzyl alcohol, and 7.9 g of triphenyl phosphine dissolved in 200 ml of dehydrated tetrahydrofuran (THF), and 15 ml of 2.2 M toluene solution of diethyl azocarboxylate was dropped for 30 minutes. After resulting solution was stirred for 5 hours at room temperature, solvent was distilled away under reduced pressure and added was 50 ml of methyl ethyl ketone. Methanol 100 ml was added to the resulting solution, and precipitated solid was filtered off. After purifying via silica gel chromatography (heptane:ethyl acetate=8:1) to obtain 11.0 g of Intermediate A (yield: 53%).

(ii) Synthesis of Intermediate B

Intermediate A 11.0 g was added to 200 ml of ethanol and replaced by nitrogen gas. After adding 1.0 g of palladium carbon, replaced by hydrogen gas and stirred for 6 hours at room temperature. After palladium carbon was filtered off, ethanol was distilled away under reduced pressure. Resulting solid was recrystallized from methyl ethyl ketone to obtain 10.4 g of Intermediate B (yield: 96%).

(iii) Synthesis of Intermediate C

Intermediate B 10.4 g was dissolved in 100 ml of dehydrated tetrahydrofuran and cooled by iced-water bath. After confirming temperature at 5° C., 1.4 g of p-iodobennzene isocyanate was added. After stirring for 30 minutes at 5° C., water was added to the resulting solution and extracted via tetrahydrofuran. Resulting organic phase was dried by sodium sulfate and solvent was distilled away under reduced pressure. Resulting solid was purified via silica gel chromatography (heptane:ethyl acetate=10:1) to obtain 10.3 g of Intermediate C (yield: 89%).

(iv) Synthesis of Compound 26

Into 100 ml of toluene, were loaded to stir 10.3 g of Intermediate C, 0.5 g of 1,6-diethynyl pyrrene and 110 ml of diethyl amine. Then, were loaded 0.03 g of copper iodide and 0.13 g of bis8triphenylphosphine palladium) chloride and heated at 50° C. After stirring for 24 hours, diethyl amine was distilled away under reduced pressure. Extraction via methylene chloride was carried out and organic phase was washed by dilute hydrogen chloride. Then, resulting organic phase was dried by sodium sulfate. Resulting solid was purified via silica gel chromatography (toluene:methylene chloride=5:1) to obtain 8.3 g of Compound 26 (yield: 41%). Product was identified by $^1$H-NMR spectra, IR spectra and mass spectra.

$^1$H-NMR spectra (CDCl$_3$, ppm): 0.88 (m. 36H), 1.26-1.41 (m. 216H), 1.76 (m, 24H), 4.06 (m, 24H), 5.10-5.18 (m, 32H), 6.59 (s, 8H), 6.92 (m, 28H), 6.99 (m, 24H), 7.57 (m, 4H), 7.71 (m, 4H), 8.02 (m, 2H), 8.08-8.20 (m, 6H), 8.75 (m, 2H)

IR spectra (ATR method, cm$^{-1}$): 3350, 3180, 1640, 1590, 1425, 1247, 1040, 784, 754, 700

Mass spectra (API method, m/e (relative strength)): 4581 ((30) MH$^+$)

Synthesizing Example 3

Synthesis of Compound 28

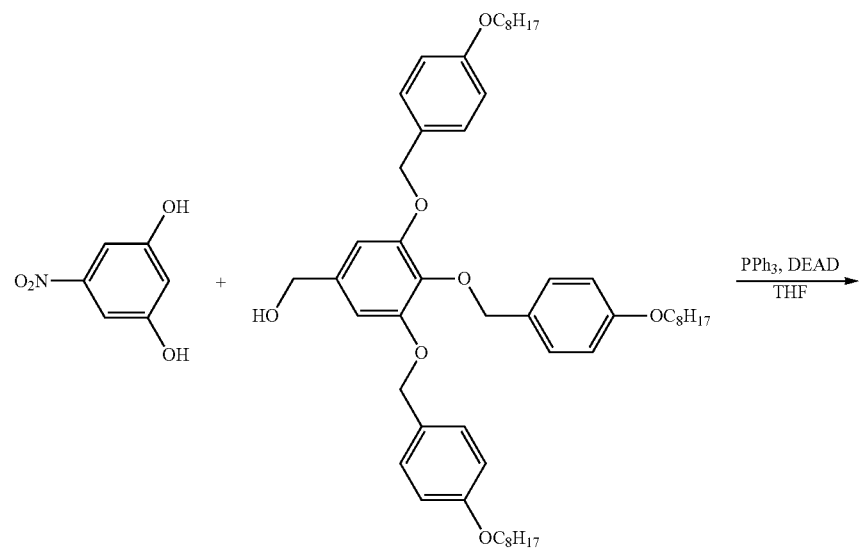

-continued
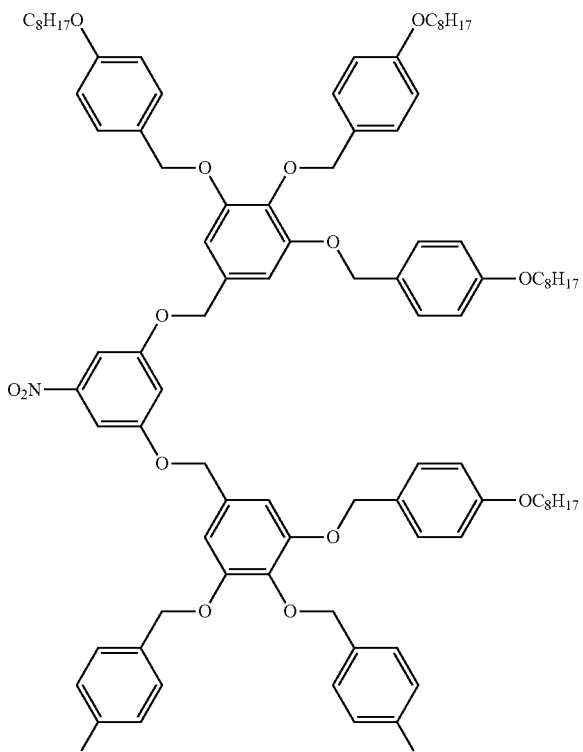
D
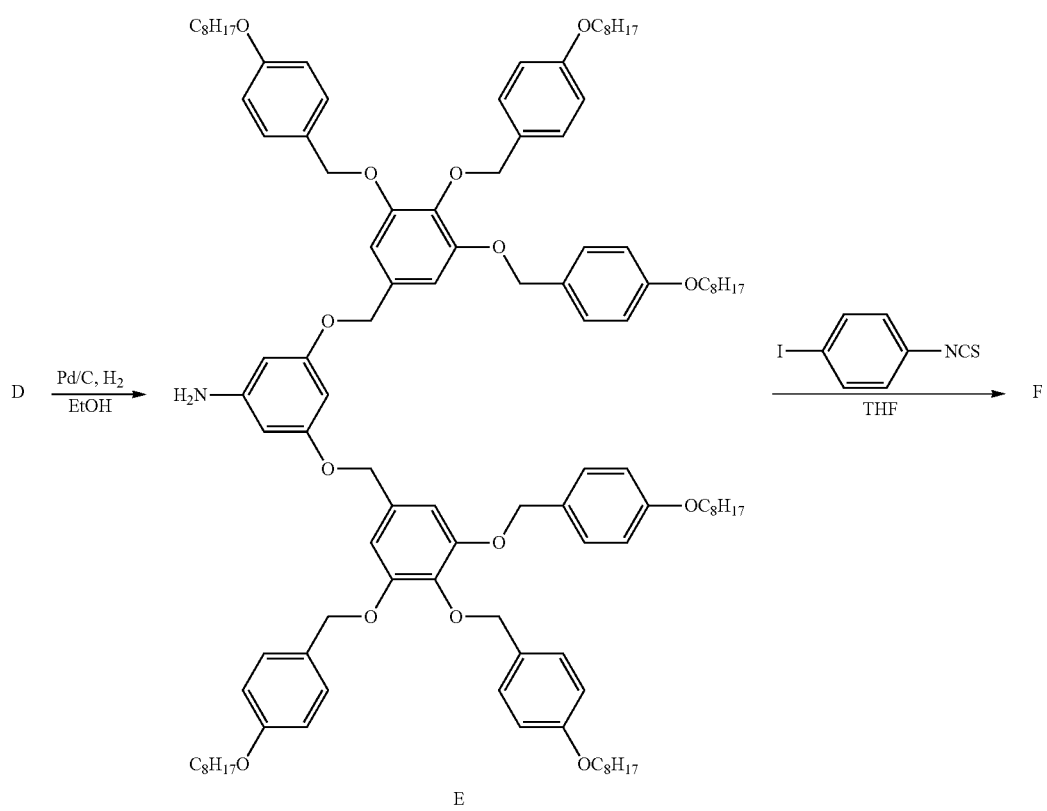
E

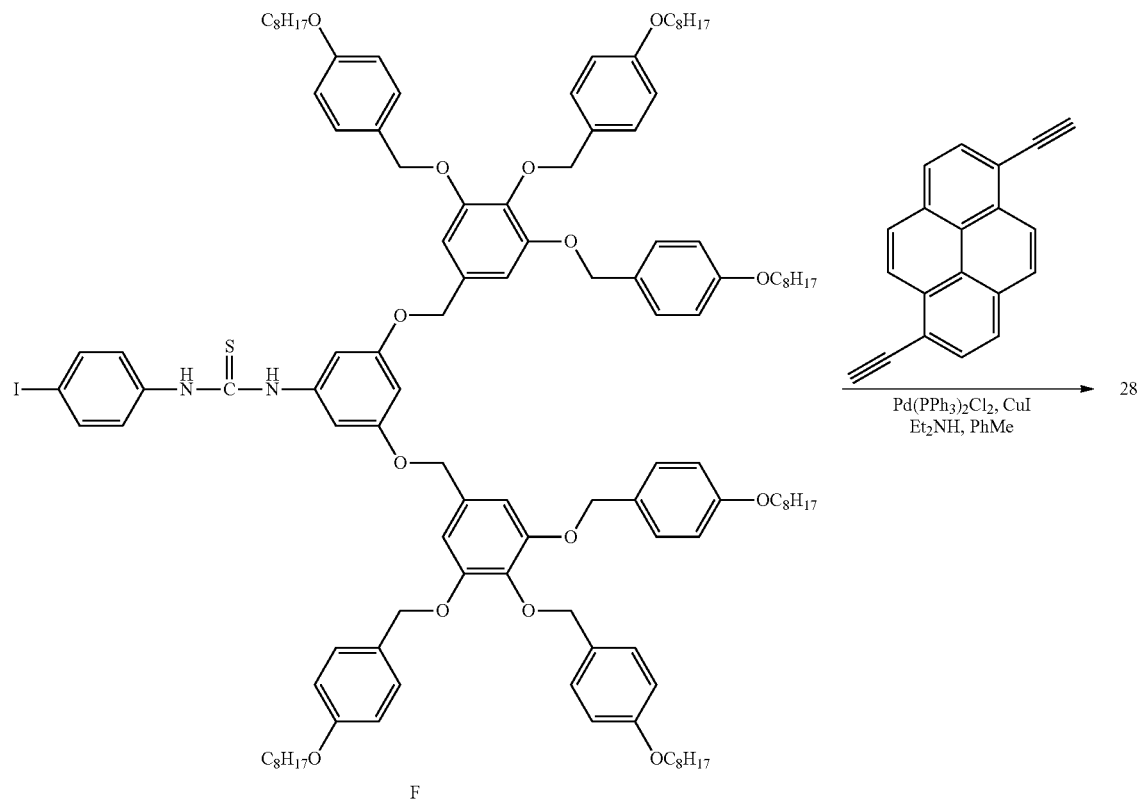
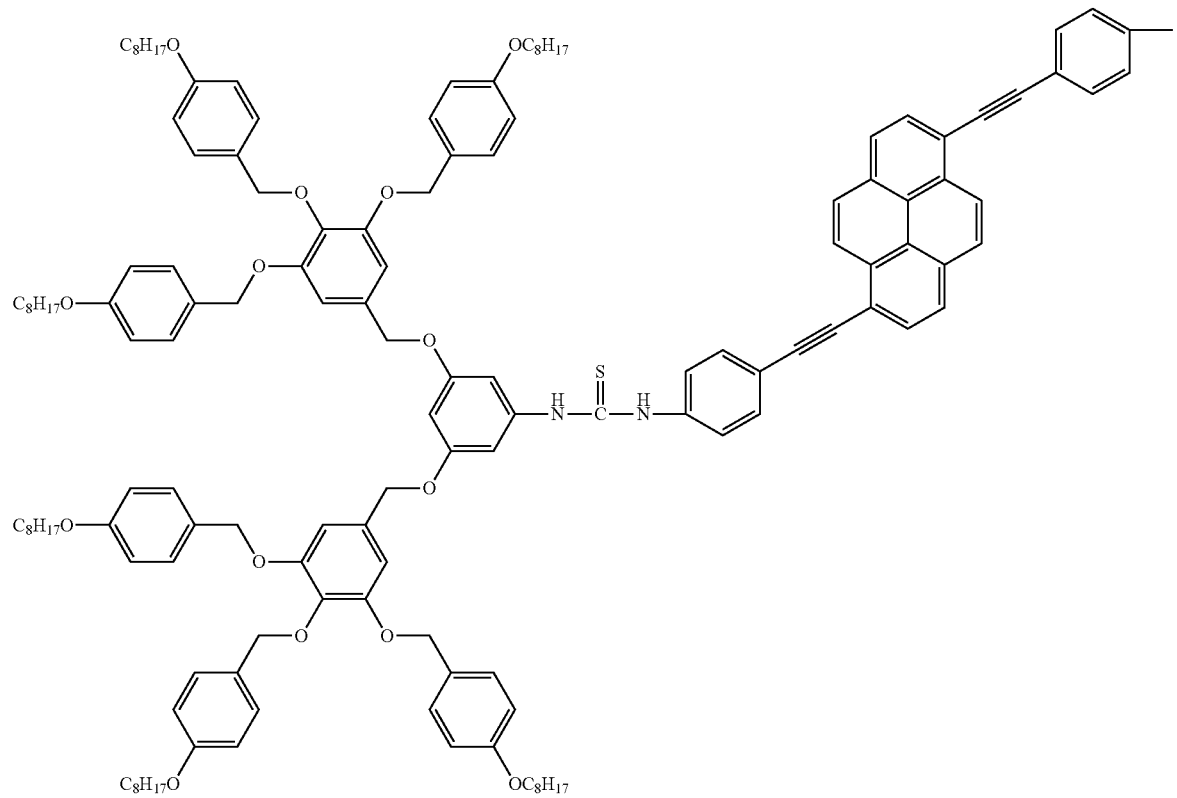

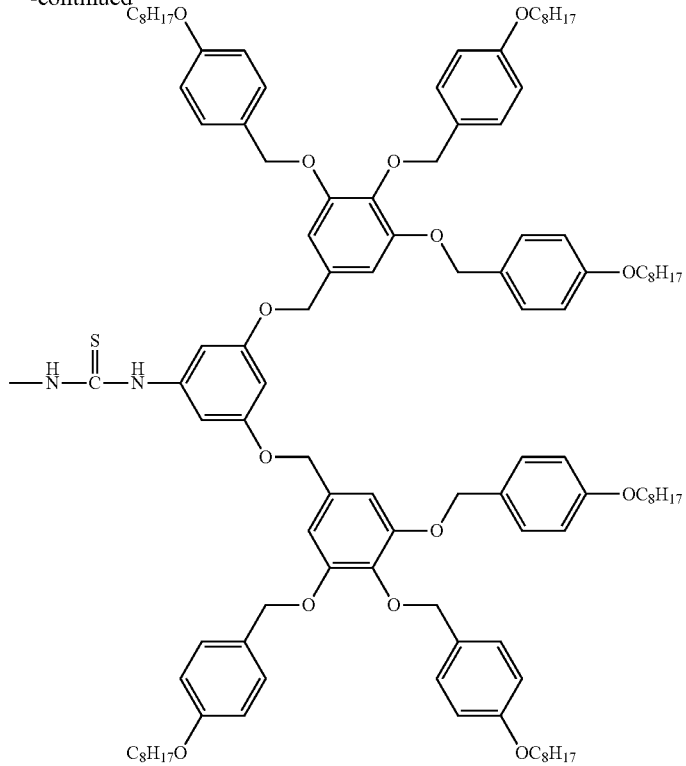

(i) Synthesis of Intermediate D

Into a reaction container replaced by nitrogen gas, were loaded 1.5 g of 2,5-dihydroxy-1-nitrobenzene, 16.6 g of 3,4,5-tris[p-(1-dehexyloxy)benzyloxy]benzyl alcohol, and 8.0 g of triphenyl phosphine dissolved in 150 ml of dehydrated tetrahydrofuran (THF), and 15 ml of DEAD (2.2 M toluene solution) was dropped for 30 minutes. After resulting solution was stirred for 3 hours at room temperature, solvent was distilled away under reduced pressure and added was 50 ml of methyl ethyl ketone. Methanol 100 ml was added to the resulting solution, and precipitated solid was filtered off. After purifying via silica gel chromatography (heptane:ethyl acetate=10:1) to obtain 8.2 g of Intermediate D (yield: 47%).

(ii) Synthesis of Intermediate E

Intermediate D 8.2 g was added to 200 ml of ethanol and replaced by nitrogen gas. After adding 0.8 g of palladium carbon, replaced by hydrogen gas and stirred for 4 hours at room temperature. After palladium carbon was filtered off, ethanol was distilled away under reduced pressure. Resulting solid was recrystallized from methyl ethyl ketone to obtain 7.9 g of Intermediate E (yield: 98%).

(iii) Synthesis of Intermediate F

Intermediate E 7.9 g was dissolved in 80 ml of dehydrated tetrahydrofuran and cooled by iced-water bath. After confirming temperature at 5° C., 1.5 g of p-iodobennzene isocyanate was added. After stirring for 20 minutes at 5° C., water was added to the resulting solution and extracted via tetrahydrofuran. Resulting organic phase was dried by sodium sulfate and solvent was distilled away under reduced pressure. Resulting solid was purified via silica gel chromatography (heptane:ethyl acetate=10:1) to obtain 7.1 g of Intermediate F (yield: 78%).

(iv) Synthesis of Compound 28

Into 150 ml of toluene, were loaded to stir 7.1 g of Intermediate F, 0.5 g of 1,6-diethynyl pyrrene and 100 ml of diethyl amine. Then, were loaded 0.03 g of copper iodide and 0.13 g of bis8triphenylphosphine palladium) chloride and heated at 50° C. After stirring for 30 hours, diethyl amine was distilled away under reduced pressure. Extraction via methylene chloride was carried out and organic phase was washed by dilute hydrogen chloride. Then, resulting organic phase was dried by sodium sulfate. Resulting solid was purified via silica gel chromatography (toluene:methylene chloride=5:1) to obtain 7.5 g of Compound 28 (yield: 53%). Product was identified by $^1$H-NMR spectra, IR spectra and mass spectra.

$^1$H-NMR spectra (CDCl$_3$, ppm): 0.88 (m. 36H), 1.29-1.41 (m. 120H), 1.78 (m, 24H), 4.01-4.07 (m, 28H), 5.16 (s, 32H), 5.74 (s. 6H), 6.59 (s, 12H), 6.92 (m, 28H), 6.98 (m, 24H), 7.34 (m, 4H), 7.71 (m, 4H), 7.96 (8.0 m, 2H), 8.02 (m, 2H)

IR spectra (ATR method, cm$^{-1}$): 3350, 1642, 1588, 1425, 1410, 1247, 1042, 780, 756

Mass spectra (API method, rule (relative strength)): 3940 ((24) MH$^+$)

Synthesizing Example 4

Synthesis of Compound 32

Dissolved was 12.0 g of 3,5-dinitro aniline to 50 ml of methanol and replaced by nitrogen gas. After adding 1.0 g of 10% palladium carbon, replaced by hydrogen gas and reacted for 2 hours under hydrogen gas atmosphere. After palladium carbon was filtered off, methanol was distilled away under reduced pressure. Then, 100 ml of tetrahydrofuran was added and the solution was replaced by nitrogen gas, and 29 ml of cyclohexyl isocyanate was dropped for 1 hour. After stirring for 3 hours at room temperature, water was added to the resulting solution and organic phase was extracted via tetrahydrofuran. Resulting organic phase was dried by sodium sulfate and solvent was distilled away under reduced pressure to obtain 28 g of compound. Resulting compound was purified via silica gel chromatography (heptane: ethyl acetate=10:1) to obtain 23.4 g of target compound 32 (yield: 78%). Product was identified by $^1$H-NMR spectra, IR spectra and mass spectra.

$^1$H-NMR spectra (CDCl$_3$, ppm): 1.08 (m. 9H), 1.28 (m, 6H), 1.40-1.53 (m. 6H), 2.39 (t, 9H), 7.12 (s, 6H), 7.88 (s, 3H)

IR spectra (ATR method, cm$^{-1}$): 3350, 3180, 1640, 1590, 1423, 1410, 756, 700

Mass spectra (API method, m/e (relative strength)): 460 ((82) MO, 415 (22)

Synthesizing Example 5

Synthesis of Compound 34

Dissolved was 12.0 g of 3,5-dinitro aniline 12.0 g to 50 ml of methanol and replaced by nitrogen gas. After adding 1.0 g of 10% palladium carbon, replaced by hydrogen gas and reacted for 2 hours under hydrogen gas atmosphere. After palladium carbon was filtered off, methanol was distilled away under reduced pressure. Then, 100 ml of tetrahydrofuran was added to dissolve, and 30.0 g of 6-ethoxyhexylamine was added. Then, 37 g of 1,1'-thiocarbonyl diimidazole was separately added for 15 minutes and stirred for 4 hours. Water was added to the resulting solution and organic phase was extracted via tetrahydrofuran. Resulting organic phase was dried by sodium sulfate and solvent was distilled away under reduced pressure to obtain 46 g of compound. Resulting compound was purified via silica gel chromatography (heptane: ethyl acetate=10:1) to obtain 37 g of target compound 34 (yield: 83%). Product was identified by $^1$H-NMR spectra, IR spectra and mass spectra.

$^1$H-NMR spectra (CDCl$_3$, ppm): 0.88 (t. 9H), 1.28-1.32 (m. 18H), 3.35 (t, 6H), 3.51 (q, 6H), 3.68 (t, 6H), 4.21 (s, 3H), 5.14 (s, 3H)

IR spectra (ATR method, cm$^1$): 3351, 3182, 1639, 1595, 1420, 1250, 759, 702

Mass spectra (API method, m/e (relative strength)): 685 ((90) MH$^+$), 553 (25)

Synthesizing Example 6

Synthesis of Compound 48

Into 5.0 g of 2,3,4,6,7,8-hexaamino anthraquinone, 50 ml of THF was added and after replacing by nitrogen gas dissolved to solution. Hexylthioisocyanate 14.3 g was dropped for 1 hour, followed by further stirring for 4 hours at room temperature. Water was added to the resulting solution and organic phase was extracted via tetrahydrofuran. Resulting organic phase was dried by sodium sulfate and solvent was distilled away under reduced pressure to obtain a compound. Resulting compound was purified via silica gel chromatography (heptane:ethyl acetate=8:1) to obtain 12.8 g of target compound 48 (yield: 66%). Product was identified by $^1$H-NMR spectra, IR spectra and mass spectra.

$^1$H-NMR spectra (CDCl$_3$, ppm): 0.86 (m. 18H), 1.28-1.34 (m. 36H), 1.50 (m, 12H), 3.02 (m, 12H), 6.04 (m, 12H), 7.86 (s, 2H)

IR spectra (ATR method, cm$^{-1}$): 3348, 3180, 1641, 1589, 1420, 759, 698

Mass spectra (API method, m/e (relative strength)): 1061 ((47) MH$^+$)

Synthesizing Example 7

Synthesis of Compound 66

Into 4.2 g of 1, 50 ml of THF was added and after replacing by nitrogen gas dissolved to solution. Thereafter, solution of 14.6 g cyclohexyl sulfonyl chloride dissolved in 100 ml THF-Hexylthioisocyanate was dropped for 1 hour, followed by further stirring for 4 hours at room temperature. Water was added to the resulting solution and organic phase was extracted via ethyl acetate. Resulting organic phase was dried by sodium sulfate and solvent was distilled away under reduced pressure to obtain a compound. Resulting compound was purified via silica gel chromatography (heptane:ethyl acetate=8:1) to obtain 7.5 g of target compound 66 (yield: 51%). Product was identified by $^1$H-NMR spectra.

$^1$H-NMR spectra (CDCl$_3$, ppm): 1.11-1.21 (m. 32H), 1.45-1.80 (m, 48H), 3.66 (m, 4H), 6.80-7.00 (m, 4H)

Example 1

Preparation of Organic Piezoelectric Material Film

Onto 25 μm of polyimide film preliminary vapor-deposited aluminum on surface, compositions comprising a compound represented by Formula (1A) and a resin compound listed in Table 8 were coated in drying thickness of 7 μm and dried to obtain Organic piezoelectric material films 1-10.

Comparable Organic piezoelectric material films 1-3 and Comparable Organic piezoelectric material films A-C were prepared in the same manner except for replacing compound represented by Formula (1A).

Evaluation of Organic Piezoelectric Material Film

Piezoelectric properties of obtained organic piezoelectric material films were evaluated via resonance method at room temperature and under heating to 100° C. Results thereof were shown in Table 8. Herein, piezoelectric properties were shown as the relative values based on the values determined at room temperature with respect to 100% for Comparable Organic piezoelectric material film A.

TABLE 8

| Organic piezoelectric material film | Compound represented by Formula (1) | CLogP(1) | Resin compound Species | Mix ratio (% by mass) | CLogP(Base material) | \|CLogP(1) - CLogP(Base material)\| | Piezoelectric property e (Relative value) Room temp. | 100° C. | Remarks |
|---|---|---|---|---|---|---|---|---|---|
| Organic piezoelectric material film-1 | 18 | 11.1 | — | — | — | — | 169 | 162 | Inv. |
| Organic piezoelectric material film-2 | 18 | 11.1 | Polystyrene (Mw = 280,000) | 10 | 11.7 | 0.6 | 162 | 158 | Inv. |
| Organic piezoelectric material film-3 | 26 | 13.3 | Polystyrene (Mw = 280,000) | 20 | 11.7 | 1.6 | 157 | 153 | Inv. |

TABLE 8-continued

| Organic piezoelectric material film | Compound represented by Formula (1) | CLogP(1) | Resin compound Species | Mix ratio (% by mass) | CLogP(Base material) | \|CLogP(1) - CLogP(Base material)\| | Piezoelectric property e (Relative value) Room temp. | 100° C. | Remarks |
|---|---|---|---|---|---|---|---|---|---|
| Organic piezoelectric material film-4 | 28 | 14.1 | Polystyrene (Mw = 280,000) | 10 | 11.7 | 2.4 | 157 | 150 | Inv. |
| Organic piezoelectric material film-5 | 18 | 11.1 | Polystyrene (Mw = 280,000) | 30 | 11.7 | 0.6 | 159 | 154 | Inv. |
| Organic piezoelectric material film-6 | 28 | 14.1 | Polystyrene (Mw = 280,000) | 30 | 11.7 | 2.4 | 155 | 151 | Inv. |
| Organic piezoelectric material film-7 | 32 | 4.2 | PVDF (Mw = 120,000) | 30 | 2.3 | 1.9 | 156 | 150 | Inv. |
| Organic piezoelectric material film-8 | 34 | 5.8 | Vinyl acetate-Styrene copolymer | 30 | 4.5 | 1.3 | 157 | 152 | Inv. |
| Organic piezoelectric material film-9 | 48 | 2.3 | PVDF (Mw = 120,000) | 40 | 2.3 | 0 | 158 | 153 | Inv. |
| Organic piezoelectric material film-10 | 66 | 12 | Polystyrene (Mw = 280,000) | 10 | 11.7 | 0.3 | 161 | 153 | Inv. |
| Comparative Organic piezoelectric material film-1 | 18 | 11.1 | PVDF (Mw = 120,000) | 30 | 2.3 | 8.8 | 150 | 132 | Comp. |
| Comparative Organic piezoelectric material film-2 | 26 | 13.3 | Vinyl acetate-Styrene copolymer | 30 | 4.5 | 8.8 | 150 | 131 | Comp. |
| Comparative Organic piezoelectric material film-3 | 32 | 4.2 | Polystyrene (Mw = 280,000) | 10 | 11.7 | 7.5 | 151 | 130 | Comp. |
| Comparative Organic piezoelectric material film-A | Comp.-A | 11.1 | — | — | — | — | 100 | 95 | Comp. |
| Comparative Organic piezoelectric material film-B | Comp.-B | 13.1 | — | — | — | — | 113 | 110 | Comp. |
| Comparative Organic piezoelectric material film-C | Comp.-A | 11.1 | Polystyrene (Mw = 280,000) | 10 | 11.7 | 0.6 | 94 | 90 | Comp. |

| No. | Polymer |
|---|---|
| Comp.-A | Triphenylene with five $OC_5H_{11}$ groups and one $COCH_3$ group |
| Comp.-B | Triphenylene with six $COOC_5H_{11}$ groups |

As is apparent from Table 8, organic piezoelectric material film formed by using the compound of the present invention exhibits excellent piezoelectric characteristic and miscibility, comparing to Comparative examples.

Example 2

Preparation and Evaluation of Ultrasound Probe (Preparation of Piezoelectric Material for Transmission)

$CaCO_3$, $La_2O_3$, $Bi_2O_3$ and $TiO_2$ were provided as component materials, and MnO as a subcomponent material. The component materials were weighed so that a final component composition was $(Ca_{0.97}La_{0.03})Bi_{4.01}Ti_4O_{15}$. Subsequently, the materials were added with pure water, mixed for 8 hours in a ball mill charged with media made of zirconia, and then sufficiently dried to obtain a mixture powder. The resulting mixture powder was temporarily molded and subjected to temporary calcination in air at 800° C. for 2 hours to obtain a preliminary calcination product. Subsequently, the preliminary calcination product was added with pure water, pulverized in a ball mill charged with media made of zirconia, and then dried to obtain a piezoelectric ceramics material powder. The pulverization time and the pulverization conditions during the pulverization being changed, a piezoelectric ceramics material powder having a particle size of 100 nm was obtained. The piezoelectric ceramics material powder having a different particle size was added with 6% by mass of pure water as a binder, and press molded to obtain a preliminary plate-like molding having a thickness of 100 μm. The resulting preliminary plate-like molding was vacuum packed and then press molded by a pressure of 235 MPa. The resulting preliminary plate-like molding was subjected to calcination to obtain a calcination product having a thickness of 20 μm as a final calcination product. The calcination temperature was 1,100° C. An electric field of not less than 1.5×Ec (MV/m) being applied for 1 minute, the calcination product was subjected to polarization treatment.

(Preparation of Laminate Transducer for Reception)

Aluminum electrode was provided by vapor deposition on the surface of the substrate of Organic piezoelectric material film-1 prepared in Example 1. Thereafter, by using high-voltage power supply apparatus HARB-20R60 (produced by Matsusada Precision Inc.), Organic piezoelectric material film-1 was heated up to 200° C. in a rate of temperature increase of 5° C./min while applying electric field of 100 MV/m. After keeping for 15 minutes at 200° C., it was stood to cool to a room temperature while applying electric field, whereby poling treatment was carried out. Resulting polarized Organic piezoelectric material film-1 was adhered to a 50 μm thick polyester film through an epoxy adhesive to obtain a laminate transducer.

Subsequently, the resulting laminate transducer for reception was laminated on the piezoelectric material for transmission described above according to an ordinary method, and further provided with a backing layer and an acoustic matching layer. Thus, an ultrasound probe was prepared. An ultrasound probe for comparison was prepared in the same manner as the ultrasound probe obtained above, except that a laminate transducer employing only Comparative organic piezoelectric material film-5 was used instead of the laminate transducer for reception.

Subsequently, the two ultrasound probes obtained above were evaluated for reception sensitivity and dielectric breakdown strength.

With regard to the reception sensitivity, a fundamental frequency $f_t$ of 5 MHz was transmitted, and then, relative reception sensitivity of a reception secondary harmonic $f_2$ of 10 MHz, a reception tertiary harmonic $f_3$ of 15 MHz and a reception quaternary harmonic $f_4$ of 20 MHz was determined. The relative reception sensitivity was measured, employing a sound intensity measuring system Model 805 (1 to 50 MHz), manufactured by Sonora Medical System, Inc., 2021 Miller Drive Longmont, Colo. (0501 USA).

After the above probes were subjected to load test in which a load power increased to five times was applied for 10 hours, relative reception sensitivity of the resulting probes was measured and evaluated as a measurement of the dielectric breakdown strength. Sensitivity, lowering by not more than 1% of that before subjected to the load test, was evaluated as good. Sensitivity, lowering by more than 1% to less than 10% of that before subjected to the load test, was evaluated as accepted. Sensitivity, lowering by not less than 10% of that before subjected to the load test, was evaluated as unacceptable.

In the above evaluation, it proved that the probe with the reception piezoelectric (material) laminate transducer of the present invention had relative reception sensitivity about 1.5 times that of the probe for comparison, and had high dielectric breakdown strength. That is, it was confirmed that the transducer for ultrasound reception of the present invention was suitably applied to a probe used in the ultrasound medical diagnostic imaging system shown in FIG. 3.

(II): the case in which the specific compound (1) is a compound represented by Formula (1B) or a polymer having a residual group of the compound represented by Formula (1B) in a side chain through $Q_1$ or $Q_2$ Example 1

Synthesis of Exemplified Compound 1

Dispersed was 63 g of silica gel into 21 g of nitric acid and 150 ml of dichloromethane was added. Into the resulting dispersion, added was a solution dissolving 10 g of 1,2,3-trihexyloxybenzene in 30 ml of dichloromethane. After stirring for 15 minutes, silica gel was filtered off. After the filtrate was concentrated under reduced pressure, 300 ml of methanol was added and stirred. Resulting precipitant was filtered off to obtain 7.3 g of 3,4,5-trihexyloxy nirobenzene (yield: 65%).

Thereafter, loaded was 7.3 g of 3,4,5-trihexyloxy nirobenzene to 3 ml of hydrazine monohydrate and 10 ml of ethanol in the presence of graphite, and reduction was carried out via heat-refluxing for 24 hours. Via recrystallized from mix solution of chloroform-methanol to obtain 4.3 g of 3,4,5-trihexyloxy aniline (yield: 63%).

Resulting 3,4,5-trihexyloxy aniline 4.3 g was dissolved in 50 ml of DNF, added was 1.3 g of N,N'-carbonyl diimidazol, and reacted for 1 hour at room temperature to obtain 2.0 g of Exemplified compound 1 (yield: 45%).

Synthesis of Exemplified Compound 2

Dispersed was 63 g of silica gel into 21 g of nitric acid and 150 ml of dichloromethane was added. Into the resulting dispersion, added was a solution dissolving 10 g of 1,2,3-tridodecyloxybenzene in 30 ml of dichloromethane. After stirring for 15 minutes, silica gel was filtered off. After the filtrate was concentrated under reduced pressure, 300 ml of methanol was added and stirred. Resulting precipitant was filtered off to obtain 7.9 g of 3,4,5-tridodecyloxy nirobenzene (yield: 74%).

Thereafter, loaded were 3 ml of hydrazine monohydrate and 10 ml of ethanol in the presence of graphite, 7.9 g of 3,4,5-tridodecyloxy nirobenzene was reduced via heat-refluxing for 24 hours. Via recrystallized from mix solution of chloroform-methanol to obtain 4.6 g of 3,4,5-tridodecyloxy aniline (yield: 60%).

Resulting 3,4,5-tridodecyloxy aniline 4.6 g was dissolved in 50 ml of DNF, added was 0.95 g of N,N'-thiocarbonyl diimidazol, and reacted for 1 hour at room temperature to obtain 2.6 g of Exemplified compound 2 (yield: 55%).

Synthesis of Exemplified Compound 3

Into 150 ml of dichloromethane controlled at 0° C., loaded were O_95 g of sulfuryl chloride and 1.4 g of triethylamine, followed by adding 0.50 g of 1,3-bis(aminomethyl)cyclohexane. Thereafter, 6.3 g of 3,4,5-trioctadecyloxy aniline synthesized in the same synthesis pathway as Exemplified compound 1 or 2 was added for 30 minutes, stirred for 1 hour at room temperature to obtain 2.8 g of Exemplified compound 3 (yield: 39%).

Synthesis of Exemplified Compound 4

Into 150 ml of pyridine controlled at 0° C., loaded was 5.0 g of 3,4,5-trioctadecyloxy aniline synthesized by (Synthesis of Exemplified Compound 3). Thereafter, 0.98 g of benzene sulfonyl chloride was added, stirred for 1 hour at room temperature to obtain 5.2 g of Exemplified compound 4 (yield: 90%).

Synthesis of Exemplified Compound 13

Dispersed was 63 g of silica gel into 21 g of nitric acid and 150 ml of dichloromethane was added. Into the resulting dispersion, added was a solution dissolving 5.0 g of 1-(1'-hydroxyoctadecyloxy)-2,3-dioctadecyloxybenzene in 30 ml of dichloromethane. After stirring for 15 minutes, silica gel was filtered off. After the filtrate was concentrated under reduced pressure, 300 ml of methanol was added and stirred. Resulting precipitant was filtered off to obtain 4.0 g of 3-(1'-hydroxyoctadecyloxy)-4,5-dioctadecyloxy nitrobenzene (yield: 76%).

Subsequently, into pyridine controlled at 0° C., dissolved was 4.0 g of 3-(1'-hydroxyoctadecyloxy)-4,5-dioctadecyloxy nitrobenzene and added 0.50 g of acryl chloride for 30 minutes, followed by stirring 1 hour at room temperature. After finishing the reaction, resulting solution was purified via silica gel chromatography (mix solvent of hexane and ethyl acetate) to obtain 3.9 g of 3-(1'-acryloyloxyoctadecyloxy)-4,5-dioctadecyloxy nitrobenzene (yield: 92%).

Thereafter, loaded were 3 ml of hydrazine monohydrate and 10 ml of ethanol in the presence of graphite, 3.9 g of 3-(1'-acryloyloxyoctadecyloxy)-4,5-dioctadecyloxy nitrobenzene was reduced via heat-refluxing for 24 hours. Via recrystallized from mix solution of chloroform-methanol to obtain 2.7 g of 3-(1'-acryloyloxyoctadecyloxy)-4,5-dioctadecyloxy aniline (yield: 71%).

Into 50 ml of DMF, dissolved was 0.58 g of 4-isothiocyanate benzyl isocyanate. Into resulting solution, added was 2.5 g of 3,4,5-trioctadecyloxy aniline synthesized by (Synthesis of Exemplified Compound 3) for 30 minutes, stirred for 1 hour at room temperature. Thereafter, added was 2.7 g of 3-(1'-acryloyloxyoctadecyloxy)-4,5-dioctadecyloxy aniline prepared above, stirred for 2 hour at room temperature. After finishing the reaction, resulting solution was purified via silica gel chromatography (mix solvent of hexane and ethyl acetate) to obtain 3.0 g of Exemplified compound 13 (yield: 51%).

Synthesis of Exemplified Compound 17

Into 100 ml of degassed toluene, added was 10 g of Exemplified compound 13. Then, resulting solution was heated at 80° C., and added was solution dissolving 7.9 mg of AIBN in 10 ml of degassed toluene for 30 minute. After finishing addition, resulting solution was further reacted for 2 hours. Thereafter, reaction solution was concentrated, purified by reprecipitation technique using hexane and methanol to obtain 9.3 g of Exemplified compound 17. Molecular weight was 20,000, and distribution of molecular weight was 15 by GPC measurement (Manufacture of Organic Piezoelectric Material Films 1-10)
Manufacture of Organic Piezoelectric Material Film Onto 25 μm of polyimide film preliminary vapor-deposited aluminum on surface, compositions comprising a compound represented by Formula (1B) and a resin compound listed in Table 9 were coated in drying thickness of 7 μm and dried to obtain Organic piezoelectric material films 1-10.

Comparable Organic piezoelectric material films 1-4 were prepared in the same manner except for replacing compound represented by Formula (113).

Evaluation of Organic Piezoelectric Material Film

Piezoelectric properties of obtained organic piezoelectric material films were evaluated via resonance method at room temperature and under heating to 100° C. Results thereof were shown in Table 9. Herein, piezoelectric properties were shown as the relative value based on the value determined at room temperature with respect to Comparable Organic piezoelectric material film 1.

TABLE 9

| Organic piezoelectric material film | Compound represented by Formula (1) | CLogP (1) | Resin compound Species | Mix ratio (% by mass) | CLogP (Base material) | \|CLogP(1) − CLogP(Base material)\| | Piezoelectric property e (Relative value) Room temp. | 100° C. | Remarks |
|---|---|---|---|---|---|---|---|---|---|
| Organic piezoelectric material film - 1 | 1 | 13.0 | Polystyrene (Mw = 280,000) | 10 | 11.7 | 1.3 | 150 | 146 | Inv. |
| Organic piezoelectric material film - 2 | 1 | 13.0 | Polystyrene (Mw = 280,000) | 20 | 11.7 | 1.3 | 134 | 134 | Inv. |
| Organic piezoelectric material film - 3 | 2 | 14.7 | Styrene-Methylstyrene copolymer (Mw = 200,000) | 10 | 12.5 | 2.2 | 151 | 148 | Inv. |
| Organic piezoelectric material film - 4 | 2 | 14.7 | Styrene-Methylstyrene copolymer (Mw = 200,000) | 30 | 12.5 | 2.2 | 132 | 129 | Inv. |

TABLE 9-continued

| Organic piezoelectric material film | Compound represented by Formula (1) | CLogP (1) | Resin compound Species | Mix ratio (% by mass) | CLogP (Base material) | \|CLogP(1) − CLogP(Base material)\| | Piezoelectric property e (Relative value) Room temp. | 100° C. | Remarks |
|---|---|---|---|---|---|---|---|---|---|
| Organic piezoelectric material film - 5 | 3 | 12.8 | Polystyrene (Mw = 280,000) | 10 | 11.7 | 1.1 | 159 | 154 | Inv. |
| Organic piezoelectric material film - 6 | 3 | 12.8 | Polystyrene (Mw = 280,000) | 30 | 11.7 | 1.1 | 132 | 127 | Inv. |
| Organic piezoelectric material film - 7 | 4 | 7.7 | Vinyl benzoate-Acrylonitrile copolymer | 30 | 5.6 | 2.1 | 126 | 120 | Inv. |
| Organic piezoelectric material film - 8 | 13 | 16.7 | Polypropylene (Mw = 100,000) | 20 | 16.0 | 0.7 | 136 | 127 | Inv. |
| Organic piezoelectric material film - 9 | 17 | 16.7 | Polypropylene (Mw = 100,000) | 10 | 16.0 | 0.7 | 148 | 144 | Inv. |
| Organic piezoelectric material film - 10 | 19 | 13.0 | Polystyrene (Mw = 280,000) | 10 | 11.7 | 1.3 | 145 | 141 | Inv. |
| Comparative Organic piezoelectric material film - 1 | 1 | 13.0 | PVDF (Mw = 120,000) | 30 | 2.3 | 10.7 | 100 | 93 | Comp. |
| Comparative Organic piezoelectric material film - 2 | 2 | 14.7 | Vinyl acetate-Styrene copolymer | 10 | 4.5 | 10.2 | 116 | 106 | Comp. |
| Comparative Organic piezoelectric material film - 3 | 17 | 16.7 | Polystyrene (Mw = 280,000) | 30 | 11.7 | 5.0 | 113 | 100 | Comp. |
| Comparative Organic piezoelectric material film - 4 | 19 | 13.0 | Vinyl acetate-Styrene copolymer | 30 | 4.5 | 8.5 | 118 | 109 | Comp. |

As is apparent from Table 9, organic piezoelectric material film formed by using the compound of the present invention exhibits excellent piezoelectric characteristic and miscibility, comparing to Comparative examples.

Example 2

Preparation and Evaluation of Ultrasound probe

<Preparation of Piezoelectric Material for Transmission>

$CaCO_3$, $La_2O_3$, $Bi_2O_3$ and $TiO_2$ were provided as component materials, and MnO as a subcomponent material. The component materials were weighed so that a final component composition was $(Ca_{0.97}La_{0.03})Bi_{4.01}Ti_4O_{15}$. Subsequently, the materials were added with pure water, mixed for 8 hours in a ball mill charged with media made of zirconia, and then sufficiently dried to obtain a mixture powder. The resulting mixture powder was temporarily molded and subjected to temporary calcination in air at 800° C. for 2 hours to obtain a preliminary calcination product. Subsequently, the preliminary calcination product was added with pure water, pulverized in a ball mill charged with media made of zirconia, and then dried to obtain a piezoelectric ceramics material powder. The pulverization time and the pulverization conditions during the pulverization being changed, a piezoelectric ceramics material powder having a particle size of 100 nm was obtained. The piezoelectric ceramics material powder having a different particle size was added with 6% by mass of pure water as a binder, and press molded to obtain a preliminary plate-like molding having a thickness of 100 μm. The resulting preliminary plate-like molding was vacuum packed and then press molded by a pressure of 235 MPa. The resulting preliminary plate-like molding was subjected to calcination to obtain a calcination product having a thickness of 20 μm as a final calcination product. The calcination temperature was 1,100° C. An electric field of not less than 1.5×Ec (MV/m) being applied for 1 minute, the calcination product was subjected to polarization treatment.

(Preparation of Laminate Transducer for Reception)

Aluminum electrode was provided by vapor deposition on the surface of a substrate of Organic piezoelectric material film-1 prepared in Example 1. Thereafter, by using high-voltage power supply apparatus HARB-20R60 (produced by Matsusada Precision Inc.), Organic piezoelectric material film-1 was heated up to 200° C. in a rate of temperature increase of 5° C./min while applying electric field of 100 MV/m. After keeping for 15 minutes at 200° C., it was stood to cool to a room temperature while applying electric field, whereby poling treatment was carried out. Resulting polarized Organic piezoelectric material film-1 was adhered to a 50 μm thick polyester film through an epoxy adhesive to obtain a laminate transducer.

Subsequently, the resulting laminate transducer for reception was laminated on the piezoelectric material for transmission described above according to an ordinary method, and further provided with a backing layer and an acoustic matching layer. Thus, an ultrasound probe was prepared. An ultrasound probe for comparison was prepared in the same manner as the ultrasound probe obtained above, except for using a laminate transducer employing only Comparative organic piezoelectric material film-5 instead of the laminate transducer for reception described above.

Subsequently, the two ultrasound probes obtained above were evaluated for reception sensitivity and dielectric breakdown strength.

With regard to the reception sensitivity, a fundamental frequency $f_1$ of 5 MHz was transmitted, and then, relative reception sensitivity of a reception secondary harmonic $f_2$ of 10 MHz, a reception tertiary harmonic $f_3$ of 15 MHz and a reception quaternary harmonic $f_4$ of 20 MHz was determined. The relative reception sensitivity was measured, employing a sound intensity measuring system Model 805 (1 to 50 MHz), manufactured by Sonora Medical System, Inc., 2021 Miller Drive Longmont, Colo. (0501 USA).

After the above probes were subjected to load test in which a load power increased to five times was applied for 10 hours, relative reception sensitivity of the resulting probes was measured and evaluated as a measure of the dielectric breakdown strength. Sensitivity, lowering by not more than 1% of that before subjected to the load test, was evaluated as good. Sensitivity, lowering by more than 1% to less than 10% of that before subjected to the load test, was evaluated as accepted. Sensitivity, lowering by not less than 10% of that before subjected to the load test, was evaluated as unacceptable.

In the above evaluation, it proved that the probe with the reception piezoelectric (material) laminate transducer of the present invention had relative reception sensitivity about 1.5 times that of the probe for comparison, and had high dielectric breakdown strength. That is, it was confirmed that the transducer for ultrasound reception of the present invention was suitably applied to a probe used in the ultrasound medical diagnostic imaging system shown in FIG. 3.

DESCRIPTION OF THE ALPHANUMERIC DESIGNATIONS

1. Piezoelectric material
2. Electrode
5. Piezoelectric material for transmission
6. Backing layer
7. Substrate
8. Acoustic matching layer
9. Acoustic lens
10. Ultrasound probe
11. Piezoelectric material for reception
12. Ultrasound transducer for transmission
13. Ultrasound transducer for reception
20. Ultrasound probe
100. Ultrasound medical diagnostic imaging system
101. Living body
102. Ultrasound probe
103. Ultrasound transducer for transmission
104. Ultrasound transducer for reception
105. Transmission and reception circuit
106. Image data conversion circuit
107. Display control circuit
108. Image display
109. Transmission and reception control circuit
110. Control circuit

What is claimed is:
1. An organic piezoelectric material comprising a compound having a substructure represented by Formula (1A) and a base material comprising a resin, wherein

CLogP(1A) and CLogP(base material) satisfies a relation represented by Equation (1), provided that CLogP(1A) represents ClogP of the compound having the substructure and CLogP(base material) represents ClogP of the base material, $$\text{Ar-(L-X-W)}_m, \quad \text{Formula (1A)}$$

wherein Ar represents an aromatic hydrocarbon ring or an aromatic heterocylic ring selected from the group consisting of a benzene ring, a naphthalene ring, a phenalene ring, a benzoquinone ring, an anthracene ring, a pyrene ring, a tricycloquinazoline ring, and a truxene ring, a tricyloquinazoline ring, and a dibenzopyrene ring, X represents —$NR_1C(=O)NR_2$—, —$NR_1C(=S)NR_2$—, —$OC(=O)O$—, —$OC(=S)O$—, —$NHC(=O)O$—, —$NHC(=S)O$—, —$NHC(=O)$—, —$NHC(=S)$—, $SO_2NH$—, or —$NHSO_2NH$—, L represents a linking group selected from the group consisting of a phenylene group, a naphthylene group a pyridilene group, and —O—$C_6H_4$—O— or a single bond, $R_1$ and $R_2$ each represents hydrogen atom or a methyl group independently, W represents a substituent group selected from the group consisting of:

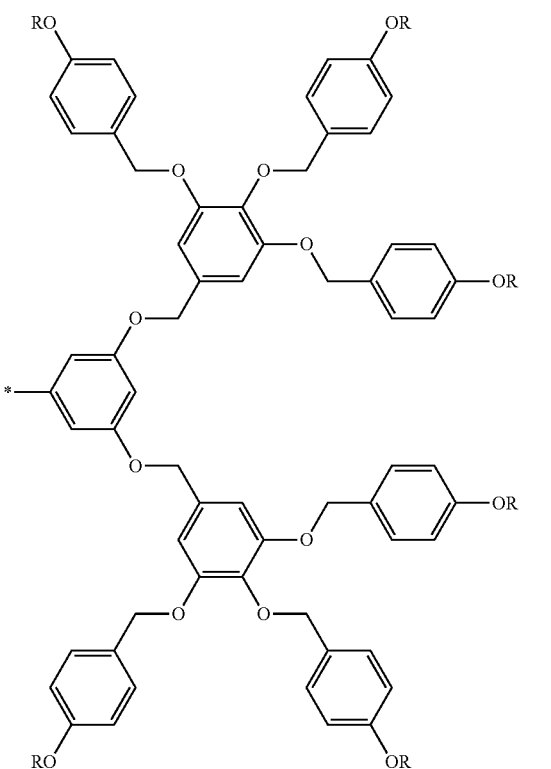

W-1

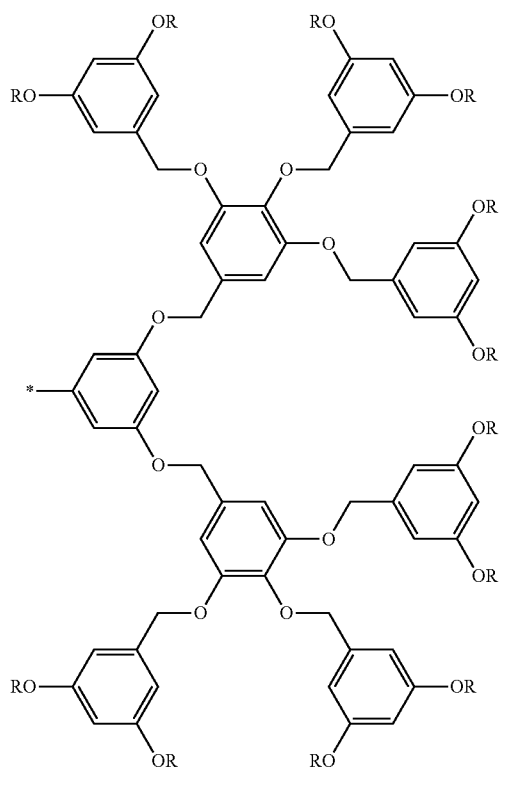

W-2

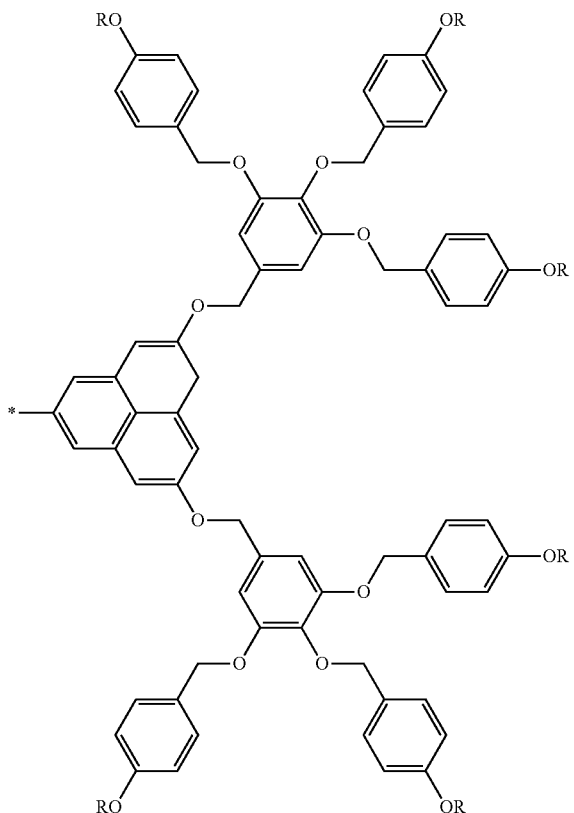

W-3

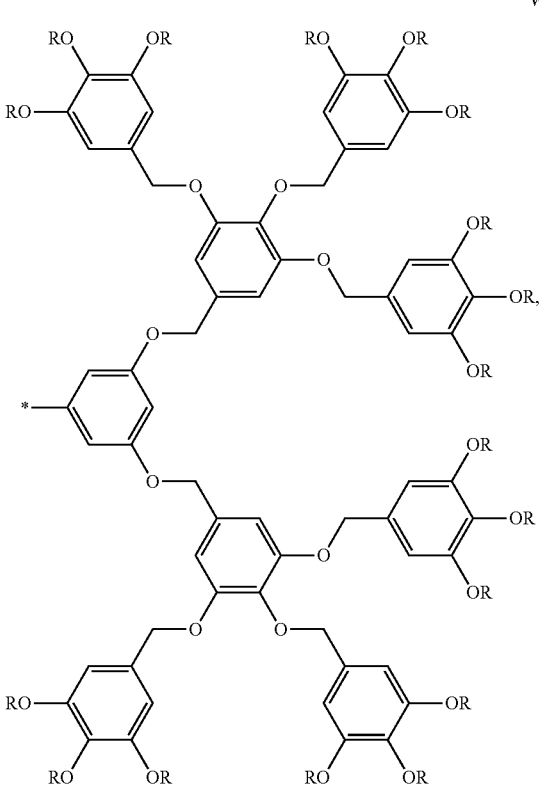

W-4

*C$_6$H$_{13}$, *CH$_2$CH$_2$OOCCF$_3$, *C$_6$H$_{12}$OC$_2$H$_5$, *C$_2$H$_4$OC$_{10}$H$_{21}$, *C$_8$H$_{17}$, *C$_{14}$H$_{29}$, *C$_6$H$_{11}$, *C$_2$H$_4$OC$_8$H$_{17}$, *C$_{12}$H$_{25}$, *C$_6$H$_5$, *C$_2$H$_4$OC$_6$H$_{13}$, *C$_4$H$_9$, *C$_2$H$_4$OC$_{12}$H$_{25}$, *CH$_2$CH(CH$_3$)C$_6$H$_{13}$, *C$_4$H$_7$, *C$_5$H$_{11}$, *CH$_2$OC$_{10}$H$_{21}$ wherein R represents an alkyl group having a carbon number of 1-20 and * represents a bond, and m represents an integer of 2-8, and $$|C\mathrm{Log}P(1A) - C\mathrm{Log}P(\text{base material})| \leq 3.0, \qquad \text{Equation (1)}$$

wherein ClogP represents "Calculated LogP" derived by Fragment approach of Hansch and Leo.

2. The organic piezoelectric material of claim 1, wherein Ar in Formula (1A) is an aromatic hydrocarbon ring or an aromatic heterocyclic ring selected from benzene, benzoquinone, anthracene, triphenylene, truxene, tricycloquinazoline and dibenzopyrene.

3. The organic piezoelectric material of claim 1, wherein L in Formula (1A) is a single bond.

4. The organic piezoelectric material of claim 1, wherein the resin constituting the base material is a thermoplastic resin, a thermosetting resin or a photo curable resin.

5. An ultrasound transducer comprising the organic piezoelectric material of claim 1.

6. An ultrasound probe providing the ultrasound transducer comprising the organic piezoelectric material of claim 1.

7. The ultrasound probe of claim 6, wherein the ultrasound transducer is an ultrasound transducer for reception.

8. An ultrasound medical diagnostic imaging system providing the ultrasound probe comprising the organic piezoelectric material of claim 1.

* * * * *